(12) United States Patent
Shiflett et al.

(10) Patent No.: US 8,075,777 B2
(45) Date of Patent: Dec. 13, 2011

(54) PROCESS FOR THE SEPARATION OF DIASTEREOMERS

(75) Inventors: Mark Brandon Shiflett, Wilmington, DE (US); Akimichi Yokozeki, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 386 days.

(21) Appl. No.: 12/120,341

(22) Filed: May 14, 2008

(65) Prior Publication Data
US 2009/0131728 A1 May 21, 2009

Related U.S. Application Data

(60) Provisional application No. 60/930,443, filed on May 16, 2007.

(51) Int. Cl.
*B01D 15/04* (2006.01)
*C02F 1/42* (2006.01)
*B01D 11/04* (2006.01)

(52) U.S. Cl. .................................. 210/638; 210/634

(58) Field of Classification Search .................. None
See application file for complete search history.

(56) References Cited

U.S. PATENT DOCUMENTS

| | | | |
|---|---|---|---|
| 4,234,544 A * | 11/1980 | Christman | .................... 422/256 |
| 5,340,555 A | 8/1994 | Mashio | |
| 5,470,442 A | 11/1995 | Mahler | |
| 5,698,750 A | 12/1997 | Mouk | |
| 5,709,092 A | 1/1998 | Shiflett | |
| 6,139,747 A * | 10/2000 | Rotzheim et al. | ............. 210/639 |
| 6,579,343 B2 | 6/2003 | Brennecke | |
| 6,843,934 B2 | 1/2005 | Bement | |
| 7,435,318 B2 | 10/2008 | Arlt | |
| 7,964,760 B2 | 6/2011 | Shiflett et al. | |
| 2002/0001560 A1 | 1/2002 | Miller | |
| 2004/0035293 A1 | 2/2004 | Davis | |
| 2006/0197053 A1 | 9/2006 | Shiflett | |
| 2006/0272934 A1 | 12/2006 | Beste | |
| 2007/0019708 A1 | 1/2007 | Shiflett | |
| 2007/0080052 A1 | 4/2007 | Beste | |
| 2007/0144186 A1 | 6/2007 | Shiflett | |
| 2007/0295478 A1 | 12/2007 | Shiflett | |
| 2007/0297965 A1 | 12/2007 | Shiflett | |
| 2008/0028777 A1 | 2/2008 | Boesmann | |
| 2008/0153697 A1 | 6/2008 | Shiflett | |
| 2008/0293978 A1 | 11/2008 | Shiflett | |
| 2009/0030235 A1* | 1/2009 | Jakel et al. | .................... 564/461 |
| 2009/0131728 A1 | 5/2009 | Shiflett | |
| 2010/0144994 A1 | 6/2010 | Shiflett | |

FOREIGN PATENT DOCUMENTS

EP 1 676 614 A1 7/2006
(Continued)

OTHER PUBLICATIONS

Shiflett et al. Solubility differences of halocarbon isomers in ionic liquid. J. Chem. Eng. Data, vol. 52 (2007) 2007-2015.*
(Continued)

*Primary Examiner* — Krishnan S Menon
*Assistant Examiner* — Katherine Zalasky

(57) ABSTRACT

A process for separating the diastereomers of a compound such as dihydrodecafluoropentane by using an ionic liquid to increase separation efficiency. The process may involve separation of the threo and erythro diastereomers of HFC-4310mee by liquid-liquid extraction wherein at least one ionic liquid is used as the extractant.

17 Claims, 12 Drawing Sheets

*Erythro*-2,3-dihydrodecafluoropentane (HFC-4310mee *Erythro*-isomer)

*Erythro* (2R,3S)

*Erythro* (2S,3R)

FOREIGN PATENT DOCUMENTS

| | | |
|---|---|---|
| WO | WO 2005/019137 A1 | 3/2005 |
| WO | WO 2007/036570 A1 | 4/2007 |
| WO | WO 2007/038363 A2 | 4/2007 |

OTHER PUBLICATIONS

Shiflett et al. Solubility and diffusivity of hydrofluorocarbons in room-temperature ionic liquids. AIChE Journal, vol. 52, No. 3 (2006) 1205-1219.*

Huddleston et al., "Room Temperature Ionic Liquids as Novel Media for Clean Liquid Liquid Extraction", Chemical Communications—Chemcom, Royal Society of Chemistry, 1998, pp. 1765-1766.

Takeuchi et al., "Resolution of DL-Valine by Countercurrent Solvent Extraction with Continuous Sample Feeding", Separation Science and Technology, vol. 25, No. 7/08, 1990, pp. 941-951.

PCT International Search Report and Written Opinion for International Application No. PCT/US2008/006221 dated Aug. 13, 2008.

Mark B. Shiflett et al, Phase Equilibria of Hydrofluorocarbon-4310mee Mixtures with Ionic Liquids: Miscibility of threo- and erythro- Diastereomers in Ionic Liquids, Industrial & Engineering Chemistry Research, vol. 47, No. 3, pp. 926-934, (2008).

Seddon, Ionic Liquids for Clean Technology, J. Chem. Tech. Biotechnol., 1997, vol. 68:351-356.

Olivier et al, Nonaqueous Room-Temperature Ionic Liquids: A New Class of Solvents for Catalytic Organic Reactions, Chem. Ind., 1996, vol. 68:249-263.

John E. Enderby, Ionic Liquids: Recent Progress and Remaining Problems, J. Phys. Condensed Matter, 1993, vol. 5:99-106.

M. Freemantle, Designer Solvents, Ionic Liquids May Boost Clean Technology Development, Chemical and Engineering News, Mar. 30, 1998, pp. 32-37.

Gordon et al, Ionic Liquid Crystals: Hexafluorophosphate Salts, J. Mater. Chem., 1998, vol. 8:2627-2636.

Welton, Room-Temperature Ionic Liquids, Solvents for Synthesis and Catalysis, Chem. Rev., 1999, vol. 99:2071-2084.

Heat Transfer, Kirk-Othmer Encyclopedia of Chemical Technology, $5^{th}$ Edition, 2005, vol. 13:242-281, John Wiley & Sons.

M.B. Shiflett et al, Solubilities and Diffusivities of Carbon Dioxide in Ionic Liquids: [bmim] [PF6] and [BF4], Ind. Eng. Chem. Res., 2005, vol. 44:4453-4464.

M.B. Shiflett et al, Solubility and Diffusivity of Hydrofluorocarbons in Room-Temperature Ionic Liquids, Aiche J., 2006, vol. 52:1205.

* cited by examiner

*Erythro*-2,3-dihydrodecafluoropentane (HFC-4310mee *Erythro*-isomer)

*Erythro* (2R,3S)          *Erythro* (2S,3R)

*Threo*-2,3-dihydrodecafluoropentane (HFC-4310mee *Threo*-isomer)

US 8,075,777 B2

PROCESS FOR THE SEPARATION OF DIASTEREOMERS

This application claims the benefit of U.S. Provisional Application No. 60/930,443, filed May 16, 2007, which is by this reference incorporated in its entirety as a part hereof for all purposes.

TECHNICAL FIELD

There is provided herein a process for separating the diastereomers of a compound by using an ionic liquid to increase separation efficiency. When the diastereomers are separated, for example, by a process such as liquid-liquid extraction, one or more ionic liquids may be used as the extractant. In one embodiment, the diastereomers of a compound such as dihydrodecafluoropentane may be separated by a process hereof.

BACKGROUND 1,1,2-Trichloro-1,2,2-trifluoroethane (CFC-113) was used for many years as a calibration fluid, as well as for cleaning applications, but its use was discontinued due to concerns linking chlorofluorocarbons (CFCs) with the depletion of ozone in the earth's atmosphere. 2,3-dihydrodecafluoropentane ($C_5H_2F_{10}$), which is also known as hydrofluorocarbon-4310mee ("HFC-4310mee"), was developed more than a decade ago as a replacement for ozone-depleting solvents such as 1,1,2-trichloro-1,2,2-trifluoroethane (CFC-113).

HFC-4310mee, which is marketed by the DuPont Company (Wilmington, Del.) under the trade name of Vertrel® XF, is typically used as an industrial cleaning and rinsing agent, drying fluid, particulate remover, solvent and dispersion medium, heat transfer fluid, or dielectric fluid. Vertrel® XF fluid was substituted for CFC-113 in many cleaning applications, but was not a good candidate as a calibration fluid because it is a mixture of the two diastereomers (HFC-4310-mee-erythro and HFC-4310-mee-threo), and does not have a constant boiling temperature at a given pressure. Also, the density of the fluid is not reproducible because the composition of the Vertrel® XF fluid is not constant. HFC-4310mee is generally not a chemically pure compound since it consists of the threo and erythro diastereomers of 2,3-dihydrodecafluoropentane ($C_5H_2F_{10}$), in addition to other impurities in some commercial formulations.

It would be advantageous to separate the threo and erythro isomers to produce a pure product containing only a single isomer. By separating the diastereomers of HFC-4310mee to produce a purified HFC-4310mee-threo or a purified HFC-4310mee-erythro product, these pure diastereomers can be used as calibration fluids for analytical instrumentation with constant boiling temperatures and known liquid density.

As a new type of solvent with immeasurable vapor pressure, room-temperature ionic liquids are being studied for diverse applications, such as chemical separations, as unique reaction media, and as environmentally friendly ("green") solvents. Several processes utilizing ionic liquids have been commercialized, such as the BASIL™ acid scavenging technology from BASF (Ludwigshafen, Germany). Although U.S. patent application Ser. No. 11/525,466 (WO 07/38363) discloses a method for using an ionic liquid to separate different compounds that are close-boiling or azeotropic components in a mixture of the compounds, a need still remains for improved processes to separate diastereomers from within a single compound.

SUMMARY

There is provided herein a process for separating one diastereomer from another diastereomer in a pair of diastereomers in a compound. In such a process, an ionic liquid may be used to facilitate the separation. In one embodiment, this separation process may be performed on a compound containing a mixture of at least one pair of diastereomers, and the diastereomers may be separated by contacting the mixture with at least one ionic liquid in which one of the diastereomers is soluble to a greater extent than the other diastereomer, and separating the lower-solubility diastereomer from the mixture. The inventions disclosed herein thus include processes for the separation of diastereomers, the use of such processes, and the products obtained and obtainable by such processes.

In another embodiment, this separation process may be performed on a compound such as dihydrodecafluoropentane wherein, in a mixture of at least one pair of diastereomers of dihydrodecafluoropentane, the diastereomers are separated by contacting the mixture with at least one ionic liquid in which one of the diastereomers is soluble to a greater extent than the other diastereomer, and separating the lower-solubility diastereomer from the mixture.

In a further embodiment, there is provided a process for separating either the HFC-4310mee threo diastereomer or the HFC-4310mee erythro diastereomer from a mixture comprising both the HFC-4310mee threo diastereomer and the HFC-4310mee erythro diastereomer comprising contacting the mixture with at least one ionic liquid in which one of the diastereomers is soluble to a greater extent than the other diastereomer, and separating the lower-solubility diastereomer from the mixture.

In yet another embodiment, there is provided a process for separating the erythro or threo diastereomers of HFC-4310mee from a mixture comprising both diastereomers by liquid-liquid extraction using at least one ionic liquid as an extractive solvent.

In yet another embodiment, there is provided a process for performing an industrial operation selected from the group consisting of a calibration operation, a cleaning operation, a rinsing operation, a drying operation, a particulate removal operation, a solvent operation, a dispersion operation, a heat transfer operation, and an insulating operation, comprising contacting a mixture comprising a pair of diastereomers of dihydrodecafluoropentane with at least one ionic liquid in which one of the diastereomers is soluble to a greater extent than the other diastereomer, separating the lower-solubility diastereomer from the mixture, and employing the separated diastereomer in the operation Each of the separated disastereomers of dihydrodecafluoropentane is useful as an industrial cleaning and rinsing agent, drying fluid, particulate remover, solvent and dispersion medium, heat transfer fluid, or dielectric fluid in the same manner as is known for Vertrel® fluid. The separated diastereomers are also useful as calibration fluids for analytical instrumentation.

Calibration fluids are high purity fluids with a constant boiling point that can be used for calibration precision temperature measuring instruments such as thermocouples and resistance temperature devices (RTDs). Calibration fluids can also be used for calibrating density instruments. For example, to determine the interior volume of a densitomer bulb, a calibration fluid with a known density at a given temperature can be used to fill the bulb and then the bulb can be accurately weighed. Knowing the density of the calibration fluid at the known temperature allows the interior of the bulb to be accurately calibrated.

The processes of this invention are thus useful for facilitating the separation of diastereomers of a compound such as dihydrodecafluoropentane, the isomers of which, as noted above, are useful for a variety of industrial purposes.

DETAILED DESCRIPTION

Figure 1:
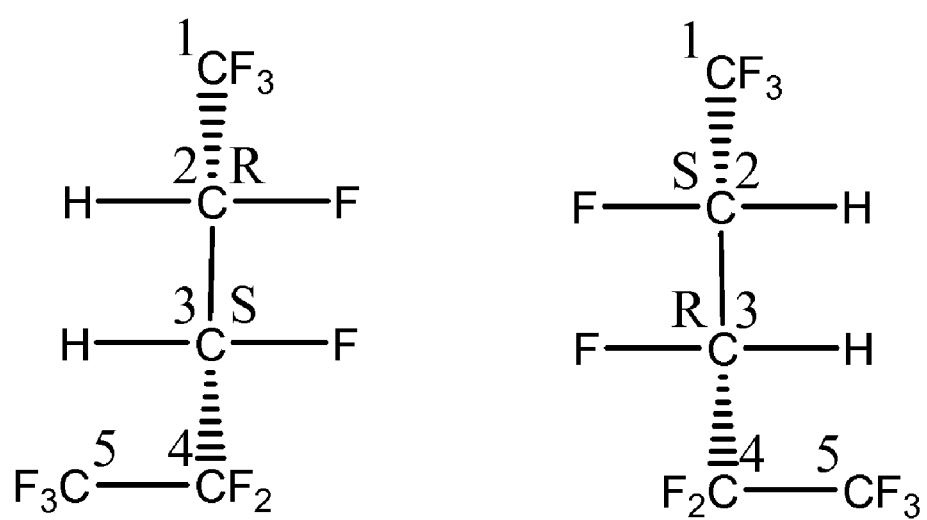
FIG. 1 shows schematic molecular structures of HFC-4310mee (erythro-2,3-dihydrodecafluoropentanes). R and S (rectus and sinister, or right and left) refer to the configuration about the chiral (asymmetric) carbon atom.

In the description of this invention, the following definitional structure is provided for certain terminology as employed variously in the specification:

The term "alkane" refers to a saturated hydrocarbon having the general formula $C_nH_{2n+2}$, which may be a straight-chain, branched or cyclic compound. A cyclic compound requires a minimum of three carbons.

The term "alkene" refers to an unsaturated hydrocarbon that contains one or more C=C double bonds, which may also be a straight-chain, branched or cyclic compound. An alkene requires a minimum of two carbons. A cyclic compound requires a minimum of three carbons.

The term "aromatic" refers to benzene and compounds that resemble benzene in chemical behavior.

A "diastereomer" is one of a pair of stereoisomers that are not mirror images of each other.

An "extractant" or "solvent" for use in liquid-liquid extraction is an immiscible liquid that, when added to a mixture, interacts with the components in the mixture in such a way that one or more, and preferably one, of the components in the mixture is less soluble in the extractant than one or more other components, thereby facilitating separation of the less soluble component or components from the mixture. The liquid phase that remains after separation of the less soluble component or components is the "extract" or "raffinate".

A "feed" to a liquid-liquid extraction process is the mixture that comprises the components to be separated.

A "fluorinated ionic liquid" is defined as an ionic liquid having at least one fluorine atom on either the cation or the anion. A "fluorinated cation" or "fluorinated anion" is a cation or anion, respectively, containing at least one fluorine atom.

"Heteroaryl" refers to an alkyl group having a heteroatom.

A "heteroatom" is an atom other than carbon in the structure of an alkanyl, alkenyl or aromatic compound.

The term "ionic liquid" is defined as an organic salt that is fluid at or below about 100° C.

"Liquid-liquid extraction" is a process for separating components in solution by their distribution between two immiscible liquid phases. Liquid-liquid extraction involves the transfer of mass from one liquid phase into a second immiscible liquid phase, and is carried out using an extractant or solvent.

"Raffinate" is the liquid phase that is left from the feed after the feed is contacted with the extractant in a liquid-liquid extraction, and one or more components are partially or completely removed from the feed mixture.

There is provided herein a process for separating one diastereomer from another diastereomer in a pair of diastereomers in a compound. In such a process, an ionic liquid is used to facilitate the separation, and the diastereomers may be separated by contacting the mixture with at least one ionic liquid in which one of the diastereomers is soluble to a greater extent than the other diastereomer, and separating the lower-solubility diastereomer from the mixture. This process may be conveniently applied to a compound such as dihydrodecafluoropentane. In a more specific embodiment, this invention relates to a process for separating diastereomers of 1,1,1,2,3,4,4,5,5,5-decafluoropentane, also known as 2,3-dihydrodecafluoropentane, or hydrofluorocarbon-4310mee ("HFC-4310mee").

Figure 2:
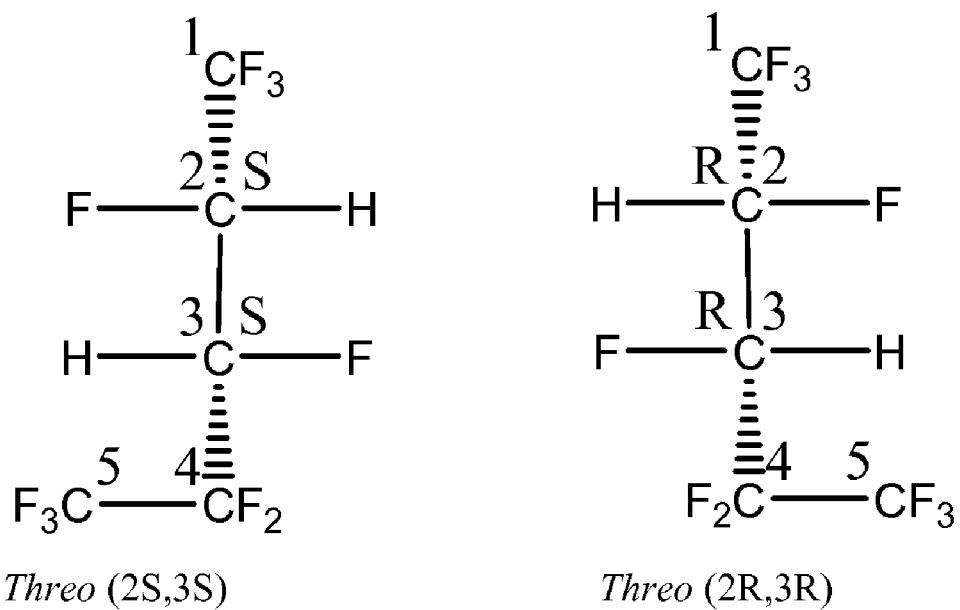
FIG. 2 shows schematic molecular structures of HFC-4310mee (threo-2,3-dihydrodecafluoropentanes). R and S (rectus and sinister, or right and left) refer to the configuration about the chiral (asymmetric) carbon atom.

Dihydrodecafluoropentane exists as a number of potential isomers, each composed of diastereomers having asymmetric (or chiral) carbon atoms. One isomer of dihydrodecafluoropentane is 2,3-dihydrodecafluoropentane, which is also known as hydrofluorocarbon-4310mee (HFC-4310mee). HFC-4310mee is composed of the threo diastereomer, also known herein as the HFC-4310-mee-threo isomer or HFC-4310mee threo, and the erythro diastereomer, also known herein as the HFC-4310mee-erythro isomer or HFC-4310mee erythro (see FIGS. 1 and 2). The threo and erythro isomers of HFC-4310mee possess two asymmetric (or chiral) carbon atoms at positions 2 and 3, and the erythro isomer is composed of the two (50/50%) optical isomers labeled (2R, 3S) and (2S, 3R), while the threo isomer is composed of the two (50/50%) optical isomers labeled (2S, 3S) and (2R, 3R). The thermophysical properties between the (2R, 3S) and (2S, 3R) optical isomers are identical, and this is similarly true for the (2S, 3S) and (2R, 3R) isomers. However, the erythro and threo isomers have significantly different thermodynamic properties; e.g. the normal boiling points are 320.1 K and 328.3 K for the former and the latter, respectively. HFC-4310mee, as available commercially, is typically a mixture of the threo (about 88 volume %) and erythro (about 12 volume %) isomers, with minor additional hydrofluorocarbon impurities (less than 1 volume %).

In one embodiment hereof, diastereomers of a compound such as dihydrodecafluoropentane can be separated by a separation process such as liquid-liquid extraction, wherein at least one ionic liquid is used as the extractant. More specifically, there is herein provided a process for separating two diastereomers in a mixture thereof by contacting the mixture with at least one ionic liquid in which one of the diastereomers is soluble to a greater extent than the other, and separating in the raffinate the lower-solubility diastereomer from the mixture, leaving behind in the extract a mixture of the extractant and the higher-solubility diastereomer.

According to one embodiment hereof, either the threo or erythro isomer of HFC-4310mee can be separated from a mixture comprising both the threo and erythro isomers by a process such as liquid-liquid extraction wherein at least one ionic liquid acts as the solvent or extractant. More specifically, there is herein provided a method for separating either the HFC-4310mee threo isomer or the HFC-4310mee erythro isomer from a mixture comprising both the HFC-4310mee threo isomer and the HFC-4310mee erythro isomer by contacting the mixture with at least one ionic liquid in which one of the diastereomers is soluble to a greater extent than the other, and separating the lower-solubility diastereomer from the mixture. In one embodiment, the HFC-4310mee erythro isomer is less soluble in an ionic liquid than the HFC-4310mee threo isomer. In an alternative embodiment, the HFC-4310mee erythro isomer is more soluble in an ionic liquid than the HFC-4310mee threo isomer. In a further embodiment, the separation is carried out at a temperature of about 280 Kelvin to about 350 Kelvin.

Components in a liquid mixture can be separated by a process such as liquid-liquid extraction using a single equilibrium (or theoretical) stage, or using multiple stages. An equilibrium, or theoretical, stage is a device that allows intimate mixing of a feed with an immiscible liquid such that concentrations approach equilibrium, followed by physical separation of the two immiscible liquid phases. A single stage device can be a separatory funnel, or an agitated vessel, which allows for intimate mixing of the feed with the immiscible extractant. Following intimate mixing, one or both of the liquid phases can be recovered, for example, by decantation.

Multiple stage devices for liquid separation can be crosscurrent or countercurrent devices. In a multiple stage device, the feed enters a first equilibrium stage and is contacted with an extractant. The two liquid phases are mixed, with droplets of one phase suspended in the second phase, and then the two phases are separated, and the raffinate from the first stage is contacted with additional extractant, and the separation process is repeated. The process of (1) contacting the raffinate with extractant, (2) allowing for equilibrium concentrations to be approached, and (3) separating the liquid phases is repeated until the desired purity of the component of interest is achieved. The number of equilibrium stages will depend on the desired purity, as well as the solubility of the components in the extractant and the flow rates of the feed and extractant.

Figure 7:
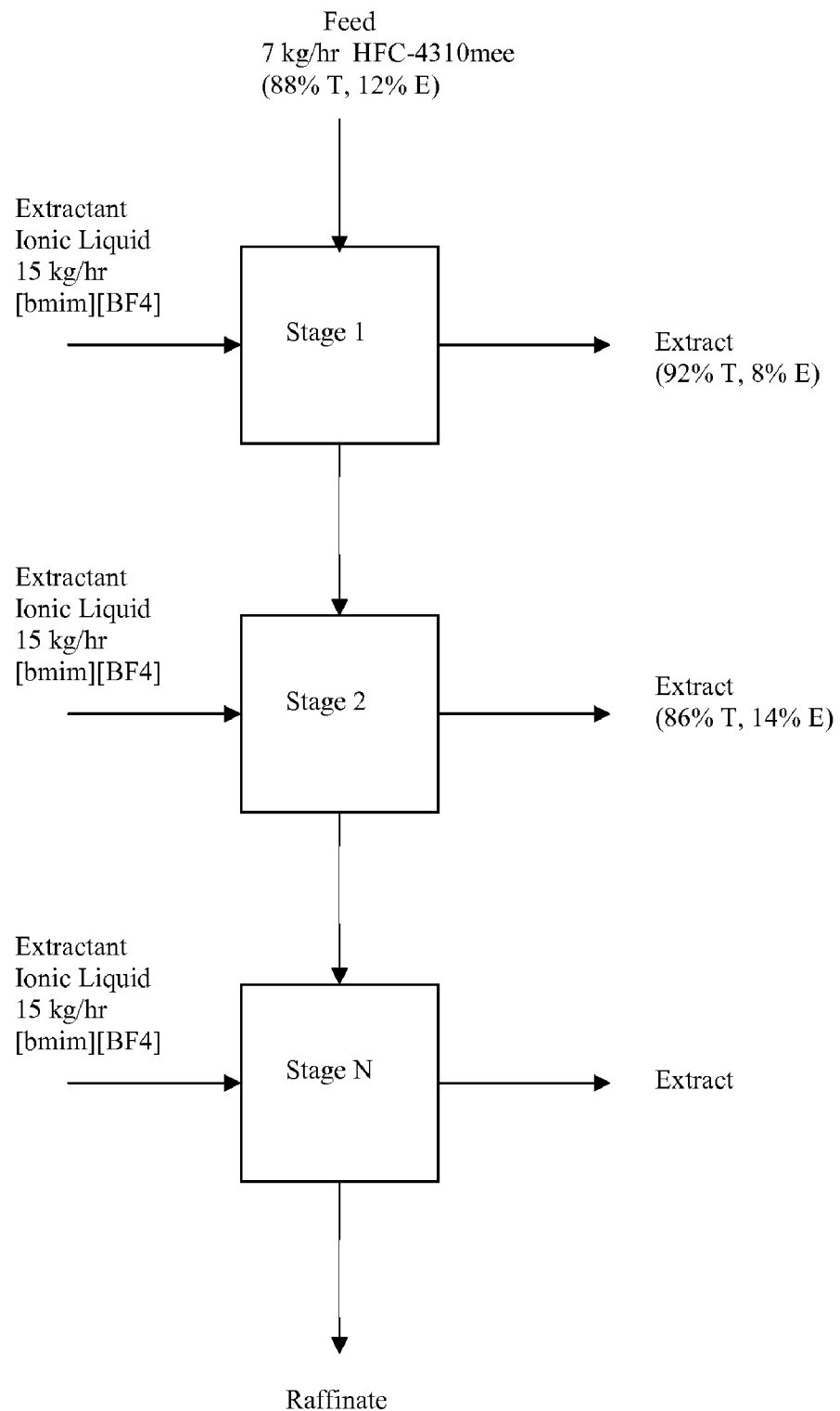
FIG. 7 shows a system for the crosscurrent extraction for separation of the erythro isomer from HFC-4310mee.

In a crosscurrent system (or device), the feed is initially contacted with extractant in a first equilibrium stage. The raffinate from this stage then cascades down through one or more additional stages. At each stage, the raffinate is contacted with fresh extractant, and further purification of the desired component in the raffinate is achieved. An example of a crosscurrent system is shown in FIG. 7, where the threo isomer of HFC-4310mee is purified using the ionic liquid 1-butyl-3-methylimidazolium tetrafluoroborate ([bmim] [$BF_4$] as the extractant.

Figure 8:
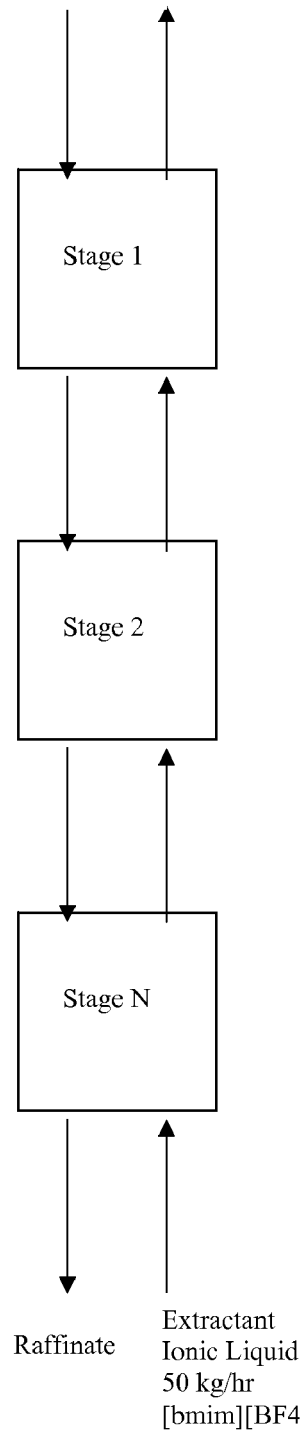
FIG. 8 shows a system for the countercurrent extraction for separation of the erythro isomer from HFC-4310mee.

In a countercurrent system (or device), the extractant enters at the stage farthest from the feed, and the two phases are passed through and across each other, coming from the two different (e.g. opposite) directions. FIG. 8 depicts the countercurrent separation of the threo and erythro isomers of HFC-4310mee from a feed thereof.

Equipment used for liquid-liquid extraction can be classified as "stagewise" or "continuous (differential) contact" equipment. Stagewise equipment is also referred to as "mixer-settlers". Mixing the liquids occurs by contacting the feed with the extractant, and the resultant dispersion is settled as the two phases separate. Mixing can occur with the use of baffles or impellers, and the separation process may be carried out in batch fashion or with continuous flow. Settlers can be simple gravity settlers, such as decanters, or can be cyclones or centrifuges, which enhance the rate of settling.

Continuous contact equipment is typically arranged for multistage countercurrent contact of the immiscible liquids, without repeated separation of the liquids from each other between stages. Instead, the liquids remain in continuous contact throughout their passage through the equipment. Countercurrent flow is maintained by the difference in densities of the liquids and either the force of gravity (vertical towers) or centrifugal force (centrifugal extractors). Gravity-operated extractors can be classified as spray towers, packed towers or perforated-plate (sieve-plate) towers. Gravity-operated towers also include towers with rotating stirrers and pulsed towers as is known in the art.

When the diastereomers of a compound such as dihydrodecafluoropentane, and in particular the threo and erythro isomers of 2,3-dihydrodecafluoropentane, are separated by a process such as liquid-liquid extraction, any of the equipment described above can be used to perform the separation. In one preferred embodiment, the separation is carried out using a vertical tower with perforated plates. After separation of the phase containing the lower-solubility diastereomer from the phase containing the extractant and the higher-solubility diastereomer, the higher solubility diastereomer may be separated from the extractant by a process such as distillation.

The transfer of mass from one liquid phase into a separate immiscible phase by liquid-liquid extraction, and equipment for use therein, is discussed further in sources such as Robbins and Cusack, "Liquid-Liquid Extraction Operations and Equipment" in *Perry's Chemical Engineers' Handbook, 7$^{th}$ Ed.*, (McGraw-Hill, 1997, Section 15). Known liquid-liquid extraction processes that operate on principles that are the same as or similar to those applicable to the separations described herein include the recovery of acetic acid from water using ethyl ether or ethyl acetate as the extractant [Brown, *Chem. Engr. Prog.* (1963) 59:65], and the recovery of phenolics from water with methyl isobutyl ketone as the extractant as described by Scheibel in "Liquid-Liquid Extraction" [Perry and Weissburg (eds), *Separation and Purification, 3$^{rd}$* Ed. (1978) Chapter 3, John Wiley & Sons, Inc., Hoboken, N.J.].

An ionic liquid, or a mixture of two or more thereof, may be used in a process hereof to separate the diastereomers of a compound. When, for example, the diastereomers of HFC-4310mee are separated by a process such as liquid-liquid extraction, the extractant used may be an ionic liquid or a mixture of two or more ionic liquids. Ionic liquids are organic compounds that are liquid at room temperature (approximately 25° C.). They differ from most salts in that they have very low melting points, and they generally tend to be liquid over a wide temperature range. They also generally tend to not be soluble in non-polar hydrocarbons; to be immiscible with water (depending on the anion); and to be highly ionizing (but have a low dielectric strength). Ionic liquids have essentially no vapor pressure, most are air and water stable, and they can either be neutral, acidic or basic.

A cation or anion of an ionic liquid useful herein can in principle be any cation or anion such that the cation and anion together form an organic salt that is liquid at or below about 100° C. The properties of an ionic liquid can, however, be tailored by varying the identity of the cation and/or anion. For example, the acidity of an ionic liquid can be adjusted by varying the molar equivalents and type and combinations of Lewis acids used.

Many ionic liquids are formed by reacting a nitrogen-containing heterocyclic ring, preferably a heteroaromatic ring, with an alkylating agent (for example, an alkyl halide) to form a quaternary ammonium salt, and performing ion exchange or other suitable reactions with various Lewis acids or their conjugate bases to form the ionic liquid. Examples of suitable heteroaromatic rings include substituted pyridines, imidazole, substituted imidazole, pyrrole and substituted pyrroles. These rings can be alkylated with virtually any straight, branched or cyclic $C_{1-20}$ alkyl group, but preferably, the alkyl groups are $C_{1-16}$ groups, since groups larger than this may produce low melting solids rather than ionic liquids. Various triarylphosphines, thioethers and cyclic and non-cyclic quaternary ammonium salts may also been used for this purpose. Counterions that may be used include chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, zinc trichloride anion, as well as various lanthanum, potassium, lithium, nickel, cobalt, manganese, and other metal-containing anions.

Ionic liquids may also be synthesized by salt metathesis, by an acid-base neutralization reaction or by quaternizing a selected nitrogen-containing compound; or they may be obtained commercially from several companies such as Merck (Darmstadt, Germany) or BASF (Mount Olive, N.J.). Representative examples of useful ionic liquids are described in sources such as *J. Chem. Tech. Biotechnol.*, 68:351-356 (1997); *Chem. Ind.*, 68:249-263 (1996); *J. Phys. Condensed Matter*, 5: (supp 34B):B99-B106 (1993); *Chemical and Engineering News*, Mar. 30, 1998, 32-37; *J. Mater. Chem.*, 8:2627-2636 (1998); *Chem. Rev.*, 99:2071-2084 (1999); and US 2004/0133058 (which is incorporated as a part hereof). In one embodiment hereof, a library, i.e. a combinatorial library, of ionic liquids may be prepared, for example, by preparing various alkyl derivatives of a particular cation (such as the quaternary ammonium cation), and varying the associated anions.

In one embodiment, ionic liquids suitable for use herein include those having cations selected from the following formulae:

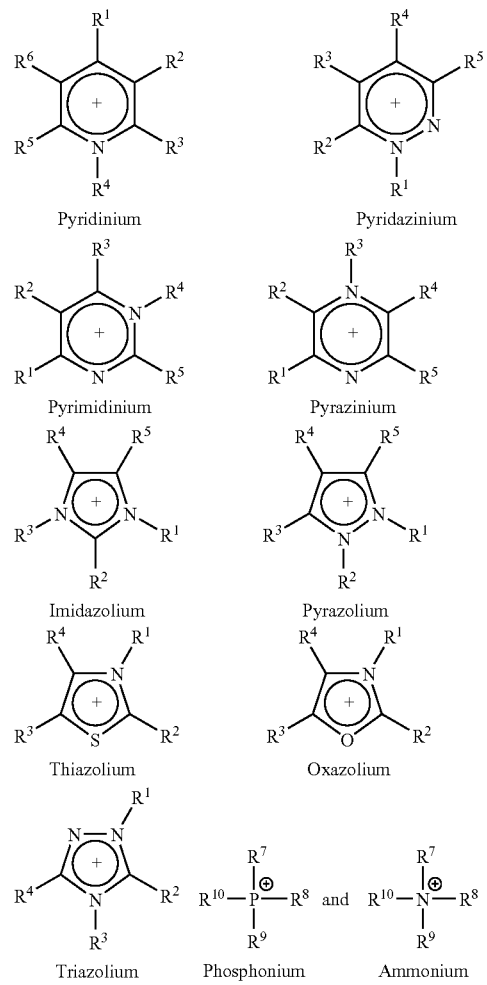

wherein $R^1$, $R^2$, $R^3$, $R^4$, $R^5$ and $R^6$ are independently selected from the group consisting of:
(i) H;
(ii) halogen;
(iii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(iv) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(v) $C_6$ to $C_{20}$ unsubstituted aryl, or $C_3$ to $C_{25}$ unsubstituted heteroaryl having one to three heteroatoms independently selected from the group consisting of O, N, Si and S; and
(vi) $C_6$ to $C_{25}$ substituted aryl, or $C_3$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:

(1) —$CH_3$, —$C_2H_5$, or $C_3$ to $C_{25}$ straight-chain, branched or cyclic alkane or alkene, optionally substituted with at least one member selected from the group consisting of Cl, Br, F I, OH, $NH_2$ and SH,
(2) OH,
(3) $NH_2$, and
(4) SH;

$R^7$, $R^8$, $R^9$ and $R^{10}$ are independently selected from the group consisting of:
(vii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(viii) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(ix) $C_6$ to $C_{25}$ unsubstituted aryl, or $C_3$ to $C_{25}$ unsubstituted heteroaryl having one to three heteroatoms independently selected from the group consisting of O, N, Si and S; and
(x) $C_6$ to $C_{25}$ substituted aryl, or $C_3$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
(1) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH,
(2) OH,
(3) $NH_2$, and
(4) SH; and
wherein, optionally, at least two of $R^1$, $R^2$, $R^3$, $R^4$, $R^5$, $R^6$, $R^7$, $R^8$, $R^9$ and $R^{10}$ together form a cyclic or bicyclic alkanyl or alkenyl group.

In another embodiment, ionic liquids useful for the invention comprise fluorinated cations wherein at least one member selected from $R^1$, $R^2$, $R^3$, $R^4$, $R^5$, $R^6$, $R^7$, $R^8$, $R^9$ and $R^{10}$ comprises $F^-$.

In another embodiment, ionic liquids useful for the invention comprise imidazolium, such as 1-ethyl-3-methylimidazolium and 1-butyl-3-methylimidazolium.

In one embodiment, ionic liquids useful herein have anions selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$; and preferably any fluorinated anion. Fluorinated anions useful herein include $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$; and $F^-$.

In a more specific embodiment, ionic liquids suitable for use herein may have a cation selected from the group consisting of pyridinium, pyridazinium, pyrimidinium, pyrazinium, imidazolium, pyrazolium, thiazolium, oxazolium, triazolium, phosphonium, and ammonium as defined above; and an anion selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, and any fluorinated anion. In yet another embodiment, ionic liquids suitable for use herein may have a cation selected from the group consisting of pyridinium, pyridazinium, pyrimidinium, pyrazinium, imidazolium, pyrazolium, thiazolium, oxazolium, triazolium, phosphonium, and ammonium as defined above; and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, and $F^-$.

In still another embodiment, ionic liquids suitable for use herein may have a cation selected from the group consisting of pyridinium, pyridazinium, pyrimidinium, pyrazinium, imidazolium, pyrazolium, thiazolium, oxazolium, triazolium, phosphonium, and ammonium as defined above, wherein at least one member selected from $R^1$, $R^2$, $R^3$, $R^4$, $R^5$, $R^6$, $R^7$, $R^8$, $R^9$, and $R^{10}$ comprises $F^-$; and an anion selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, and any fluorinated anion. In still another embodiment, ionic liquids suitable for use herein may have a cation selected from the group consisting of pyridinium, pyridazinium, pyrimidinium, pyrazinium, imidazolium, pyrazolium, thiazolium, oxazolium, triazolium, phosphonium, and ammonium as defined above, wherein at least one member selected from $R^1$, $R^2$, $R^3$, $R^4$, $R^5$, $R^6$, $R^7$, $R^8 R^9$, and $R^{10}$ comprises $F^-$; and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, and $F^-$.

In one embodiment, the ionic liquid comprises imidazolium as the cation and $[BF_4]^-$ or $[PF_6]^-$ as the anion. In a more specific embodiment, the ionic liquid comprises 1-ethyl-3-methylimidazolium or 1-butyl-3-methylimidazolium as the cation, and $[BF_4]^-$ or $[PF_6]^-$ as the anion.

In various embodiments of this invention, an ionic liquid formed by selecting any of the individual cations described or disclosed herein, and by selecting any of the individual anions described or disclosed herein with which to pair the cation, may be used for the purpose of separating diastereomers. Correspondingly, in yet other embodiments, a subgroup of ionic liquids formed by selecting (i) a subgroup of any size of cations, taken from the total group of cations described and disclosed herein in all the various different combinations of the individual members of that total group, and (ii) a subgroup of any size of anions, taken from the total group of anions described and disclosed herein in all the various different combinations of the individual members of that total group, may be used for the purpose of separating diastereomers. In forming an ionic liquid, or a subgroup of ionic liquids, by making selections as aforesaid, the ionic liquid or subgroup will be used in the absence of the members of the group of cations and/or anions that are omitted from the total group thereof to make the selection, and, if desirable, the selection may thus be made in terms of the members of the total group that are omitted from use rather than the members of the group that are included for use.

The following examples are presented to illustrate the operation and advantages of the present invention, and to assist the reader in making and using the same. These examples are not intended in any way to limit the scope of the disclosure or the appended claims.

General Materials and Methods

The following abbreviations are used: kPa is kilo Pascal; K is Kelvin, °C. is degrees Centigrade; mm is millimeter; cm is centimeter; g is gram; h is hour; ppm is parts per million; and mol is mole.

HFC-4310mee was obtained as a sample of Vertrel® XF fluid as commercially available from the DuPont Company (Wilmington, Del.). The HFC-4310mee threo-isomer (threo-H), and erythro-isomer (erythro-H) were separated from the sample using a spinning-band distillation column. Deuterated threo-isomer (threo-D) and deuterated erythro-isomer (erythro-D) were specially prepared from the purified threo-H and erythro-H isomers. The purity of the HFC-4310mee sample and of the resulting isomers was determined by gas chromatography mass spectrometry (GCMS). The sample of HFC-4310mee was composed of 87.12±0.6% threo-H, 11.89±0.6% erythro-H and less than 1.0% of other minor HFC impurities such as $C_6H_2F_{12}$, $C_5H_3F_9$ and $C_4H_2F_8$. All purified isomers had purities of >99.9%.

The following ionic liquids: 1-Butyl-3-methylimidazolium hexafluorophosphate ([bmim][$PF_6$], $C_8H_{15}N_2F_6P$, molecular weight 284.18 g $mol^{-1}$), 1-butyl-3-methylimidazolium tetrafluoroborate ([bmim][$BF_4$], $C_8H_{15}N_2F_4B$, molecular weight 226.13 g $mol^{-1}$), and 1-ethyl-3-methylimidazolium tetrafluoroborate ([emim][$BF_4$], $C_6H_{11}N_2F_4B$, molecular weight 197.98 g $mol^{-1}$) were obtained from Fluka Chemika (may be obtained from Sigma-Aldrich, St. Louis, Mo.) with a purity of >97%. The ionic liquid samples were dried and degassed by first placing the samples in borosilicate glass tubes and pulling a coarse vacuum on the samples with a diaphragm pump (Pfeiffer, model MVPO055-3, Nashua, N.H.) for about 3 h. Next, the samples were fully evacuated using a turbopump (Pfeiffer, model TSH-071) to a pressure of about $4\times10^{-7}$ kPa while simultaneously heating and stirring the ionic liquids at a temperature of about 348 K for 48 to 96 h. The mass fractions of water remaining in the dried samples were measured by Karl Fischer titration (Aqua-Star C3000, solutions AquaStar Coulomat C and A) and were 363, 272, and 207 ppm for [bmim][$PF_6$], [bmim][$BF_4$], and [emim][$BF_4$], respectively.

The preparation of the following compounds for use as an anionic component in an ionic liquid:
  potassium 1,1,2,2-tetrafluoroethanesulfonate,
  potassium-1,1,2-trifluoro-2-(perfluoroethoxy)ethanesulfonate,
  potassium-1,1,2-trifluoro-2-(trifluoromethoxy)ethanesulfonate, and
  sodium 1,1,2,3,3,3-hexafluoropropanesulfonate); and
the preparation of the following materials, which are suitable for use as an ionic liquid in the process of this invention:
  1-butyl-2,3-dimethylimidazolium 1,1,2,2-tetrafluoroethanesulfonate,
  1-butyl-methylimidazolium 1,1,2,2-tetrafluoroethanesulfonate,
  1-ethyl-3-methylimidazolium 1,1,2,2-tetrafluoroethanesulfonate,
  1-ethyl-3-methylimidazolium 1,1,2,3,3,3-hexafluoropropanesulfonate,
  1-hexyl-3-methylimidazolium 1,1,2,2-tetrafluoroethanesulfonate,
  1-dodecyl-3-methylimidazolium 1,1,2,2-tetrafluoroethanesulfonate,
  1-hexadecyl-3-methylimidazolium 1,1,2,2-tetrafluoroethanesulfonate,
  1-octadecyl-3-methylimidazolium 1,1,2,2-tetrafluoroethaneulfonate,
  1-propyl-3-(1,1,2,2-TFES) imidazolium 1,1,2,2-tetrafluoroethanesulfonate,
  1-butyl-3-methylimidazolium 1,1,2,3,3,3-hexafluoropropanesulfonate,
  1-butyl-3-methylimidazolium 1,1,2-trifluoro-2-(trifluoromethoxy)ethanesulfonate,
  1-butyl-3-methylimidazolium 1,1,2-trifluoro-2-(perfluoroethoxy)ethanesulfonate,
  tetradecyl(tri-n-butyl)phosphonium 1,1,2,3,3,3-hexafluoropropanesulfonate,
  tetradecyl(tri-n-hexyl)phosphonium 1,1,2-trifluoro-2-(perfluoroethoxy)ethanesulfonate,
  tetradecyl(tri-n-hexyl)phosphonium 1,1,2-trifluoro-2-(trifluoromethoxy)ethanesulfonate,
  1-ethyl-3-methylimidazolium 1,1,2,2-tetrafluoro-2-(pentafluoroethoxy) sulfonate, and
  tetrabutylphosphonium 1,1,2-trifluoro-2-(perfluoroethoxy)ethanesulfonate) may be performed in the manner described in U.S. patent application Ser. No. 11/525,466, which is by this reference incorporated in its entirety as a part hereof for all purposes.

The separation of the erythro or threo diastereomer from a mixture thereof in HFC-4310mee involves one of the diastereomers being soluble to a greater extent in at least one ionic liquid than the other diastereomer is. In order to study this type of behavior, liquid-liquid equilibrium (LLE) and cloud point measurements on samples of HFC-4310mee were made as described in Examples 1 to 4. Principles applicable to a study of these kinds of systems include the thermodynamic constraint, the univariant state (Gibbs phase rule), and the mass balance, as described in Shiflett, M. B. and Yokozeki, A. (Vapor-liquid-liquid equilibria of pentafluoroethane and ionic liquid [bmim][$PF_6$] mixtures studied with the volumetric method, J. Phys. Chem. B (2006) 110:14436-14443; and Shiflett, M. B. and Yokozeki, A. (Vapor-liquid-liquid equilibria of hydrofluorocarbons+1-butyl-3-methylimidazolium hexafluorophosphate, J. Chem. & Eng. Data (2006) 51:1931-1939).

Low-pressure sample containers were fabricated from borosilicate glass tubing with an outside diameter of 12.69 mm, an inside diameter of 7.94 mm, and an overall length of 15.5 cm. The glass tubing was sealed with a torch on one end and open on the other. The volume of each liquid layer was obtained by measuring the liquid height from the bottom of the glass tubing using an electronic caliper (Mitutoyo Corp., model no. CD-6" CS, code no. 500-196, Aurora, Ill.). The volume, v, versus the height, h, was calibrated experimentally using methyl alcohol and a linear relation was obtained. The sample containers were initially weighed to determine the tare mass. The samples were then prepared in a nitrogen purged dry box to minimize water contact with the hygroscopic ionic liquids. A glass pipette was used to add the required amounts of ionic liquid and HFC-4310mee. Two samples containing, respectively, about 35 and 90 mole % HFC-4310mee in [bmim][$PF_6$] were prepared. Similar molar compositions were also prepared using [bmim][$BF_4$] and [emim][$BF_4$]. A Swagelok® (Solon, Ohio) stainless steel (SS316) cap and plug with poly(tetrafluoroethylene) ferrules was used to seal the open end of the glass tubing before removing the tubing from the dry box.

Initially, the samples were mixed at room temperature (293.2 K) by vigorously shaking the sample containers. In this system, the upper liquid phase is the ionic liquid-rich phase and the lower liquid phase is HFC-4310mee liquid-rich phase. To establish the thermodynamic equilibrium, sufficient time and mixing are required. A custom-made mixing apparatus, which can hold 14 sample containers, was designed for rocking the tubes back and forth inside a water-filled Plexiglas tank, and the temperature was controlled with an external temperature bath (PolyScience, model 1190S, Niles, Ill.) which circulated water through a copper coil inside the tank. The water bath was stirred with an agitator (Arrow Engineering Co., Inc. model 1750, Hillside, N.J.) and the temperature measured with a thermocouple (Fluke Corporation, model 5211 thermometer, Everett, Wash.). The Fluke thermometer was calibrated using a standard platinum resistance thermometer (SPRT model 5699, Hart Scientific, American Fork, Utah, range 73 to 933 K) and readout (Blackstack model 1560 with SPRT module 2560). The Blackstack instrument and SPRT are also a NIST certified secondary temperature standard.

The water bath temperature was initially set at about 283 K, and the sample containers were rocked back and forth. Before height measurements were taken, the sample holder was positioned upright below the water level of the tank for 6 to 12 h. The volume of each liquid layer was obtained by measuring the liquid height from the bottom of the glass tube using the electronic caliper. The mixing and measurement procedure was repeated each day and the heights plotted as a function of time until no further change in the heights was detected. The objective of the experiments was to establish the equilibrium state, and using this procedure required 3 to 5 days to reach equilibrium at 283 K. These experiments were repeated at various temperatures up to about 333 K. To ensure no leaks occurred during the LLE experiments, the weights of the sample containers were checked after completing all measurements and compared with the original weights.

In order to demonstrate the existence of a lower critical solution temperature (LCST) of the liquid-liquid equilibrium (LLE) curve, cloud-point measurements were made with samples prepared using the threo-H and threo-D isomers with [bmim][$PF_6$], [bmim][$BF_4$], and [emim][$BF_4$]. Starting at ambient temperature of about 293 K, where two liquid phases existed, the temperature was lowered (20 K/h) with manual mixing in a constant temperature bath (Tamson Instruments, TV4000LT, Zoetermeer, Netherlands) until only a single phase existed. The bath temperature was calibrated with the NIST traceable SPRT mentioned previously. Achieving a single phase with the mixtures prepared using [emim][$BF_4$] involved going to a lower temperature than was required to achieve a single phase with the mixtures prepared using [bmim][$PF_6$] and [bmim][$BF_4$]. In addition, the rate of decrease in temperature had to be decreased from 20 to 5 K/h with vigorous manual mixing to prevent the ionic-liquid rich phase from solidifying. Sufficient time with vigorous mixing allowed for mixtures containing 70 mole % and higher threo-H and threo-D isomers with [emim][$BF_4$] to become a single phase at a temperature of 240 K. Once the samples were single phase the temperature was slowly raised 2 K/h until a cloud layer became visible inside the tube. The temperature was recorded for each sample when the cloud layer formed and the temperature was slowly raised until all samples had reached the cloud point.

The final equilibrium results for the molar compositions and volumes are provided in Examples 1 to 3, and in Tables 1 to 3. The observed cloud points for HFC-4310mee threo-isomer (Threo-H) and deuterated threo-isomer (Threo-D) with ionic liquids [bmim][$PF_6$], [bmim][$BF_4$], and [emim][$BF_4$] are provided in Table 4.

Observed LLE data have been correlated with the NRTL (non-random two liquid) solution model as described in Shiflett, M. B. and Yokozeki, A. (Vapor-liquid-liquid equilibria of pentafluoroethane and ionic liquid [bmim][$PF_6$] mixtures studied with the volumetric method, *J. Phys. Chem. B* (2006) 110:14436-14443); and in Shiflett, M. B. and Yokozeki, A. (Vapor-liquid-liquid equilibria of hydrofluorocarbons+1-butyl-3-methylimidazolium hexafluorophosphate, *J. Chem. & Eng. Data* (2006) 51:1931-1939).

The binary activity coefficients of the NRTL are given by:

$$\ln\gamma_1 = x_2^2\left[\tau_{21}\left(\frac{G_{21}}{x_1 + x_2 G_{21}}\right)^2 + \frac{\tau_{12} G_{12}}{(x_2 + x_1 G_{12})^2}\right], \quad (1)$$

$$\ln\gamma_2 = x_1^2\left[\tau_{12}\left(\frac{G_{12}}{x_2 + x_1 G_{12}}\right)^2 + \frac{\tau_{21} G_{21}}{(x_1 + x_2 G_{21})^2}\right], \quad (2)$$

where $$G_{12} \equiv \exp(-\alpha\tau_{12}), \text{ and } G_{21} \equiv \exp(-\alpha\tau_{21}) \quad (3)$$

$$\tau_{12} \equiv \frac{\Delta g_1}{RT}, \quad (4)$$

and $$\tau_{21} \equiv \frac{\Delta g_2}{RT}: \text{ (adjustable binary interaction parameters)}.$$

$\alpha=0.2$ (assumed to be a constant of 0.2 in this work).
$x_i$=mole fraction of the i-th species.

The temperature-dependent binary interaction parameter ($\tau_{ij}$) is modeled here by a three term empirical equation:

$$\tau_{12} = \tau_{12}^{(0)} + \tau_{12}^{(1)}/T + \tau_{12}^{(2)}T, \text{ and } \tau_{21} = \tau_{21}^{(0)} + \tau_{21}^{(1)}/T + \tau_{21}^{(2)}T \quad (5)$$

The binary LLE (L1 for liquid 1 and L2 for liquid 2) are mathematically described by the following equilibrium condition:

$$\gamma_i^{L1} x_i^{L1} = \gamma_i^{L2} x_i^{L2} \quad (6)$$

Thus, the two adjustable parameters $\tau_{12}$ and $\tau_{21}$ at a given T can be determined from one set of LLE experimental (volumetric method) data, using eq 6 (two nonlinearly coupled equations). We obtained several sets of such LLE data and can obtain $\tau_{12}$ and $\tau_{21}$ at respective T. Then, the empirical parameters in eq 5 were determined and are shown in Example 5, Table 5, where results for only the non-deuterated isomers with ionic liquids are given, since results for the deuterated isomer cases are similar to those in Table 5.

Once the binary interaction parameters of the NRTL model have been determined as a function of temperature, the Tx (temperature-composition) phase diagram can be calculated by solving eq 6. A flash algorithm was used to solve the phase equilibrium condition. Calculated Tx diagrams are compared with the experimental solubility data in FIGS. 3-5. All threo isomer systems with the ionic liquids show LCSTs (lower critical solution temperatures): 265-267 K at about 70 (threo-isomer) mole %, and 307-309 K at about 75 mole % for [bmim][$PF_6$] and [bmim][$BF_4$] systems, respectively. In the case of the threo+[emim][$BF_4$] system, the LCST is about 250 K at near 50 mole %.

Figure 3A:
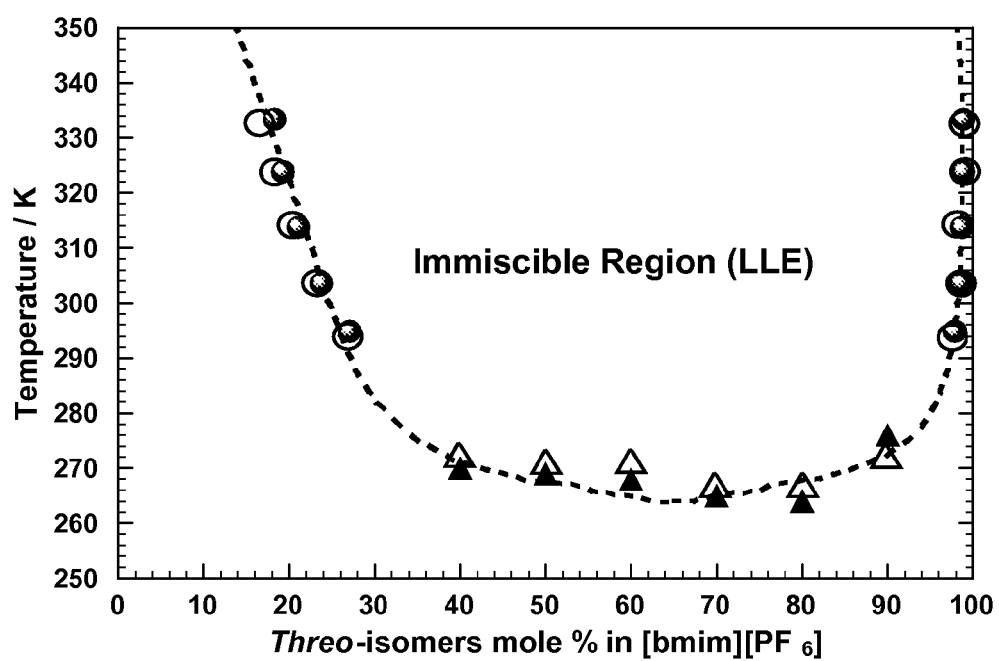
FIG. 3 shows Tx phase diagrams for liquid-liquid equilibrium ("LLE"). Broken line: calculated with the non-random two liquid ("NRTL") activity model for non-deuterated species. Symbols: experimental data; solid symbols=non-deuterated species; open symbols=deuterated species; circles=LLE experiments and triangles=the cloud-point method. (a) Threo+[bmim][$PF_6$] system. (b) Erythro+[bmim][$PF_6$] system.
Figure 3B:
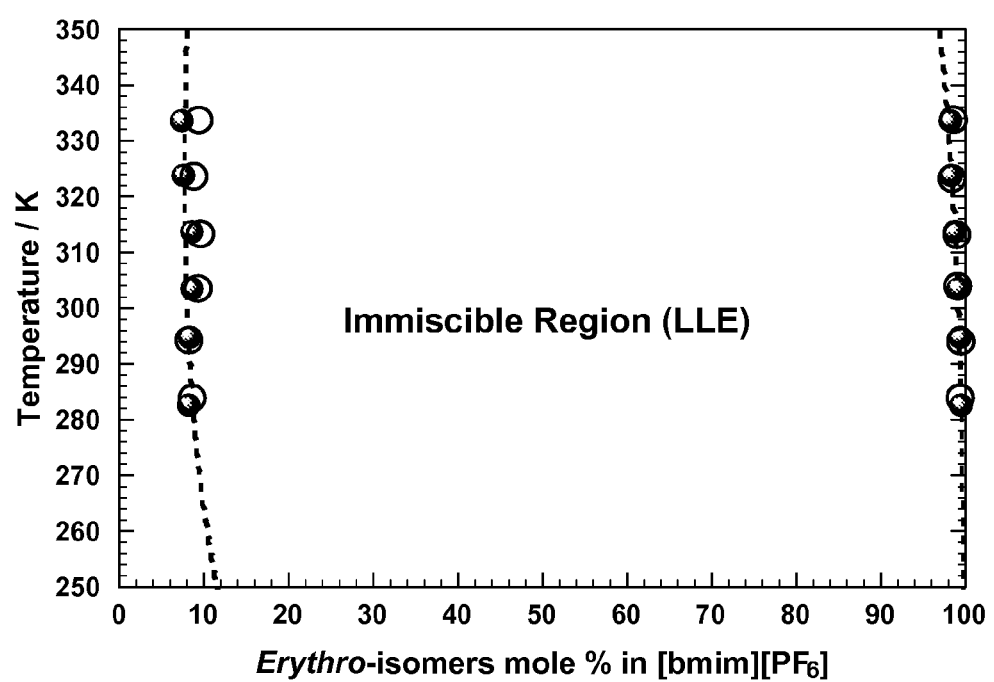
Figure 4A:
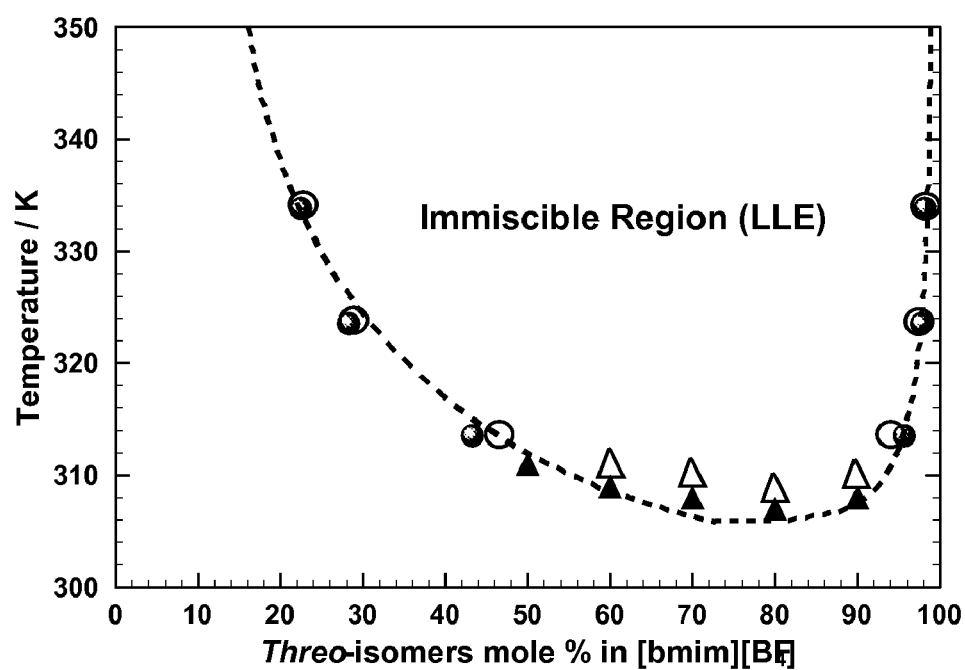
FIG. 4 shows Tx phase diagrams for LLE. Broken line: calculated with the NRTL activity model for non-deuterated species. Symbols: experimental data; solid symbols=non-deuterated species; open symbols=deuterated species; circles=LLE experiments and triangles=the cloud-point method. (a) Threo+[bmim][$BF_4$] system. (b) Erythro+[bmim][$BF_4$] system.
Figure 4B:
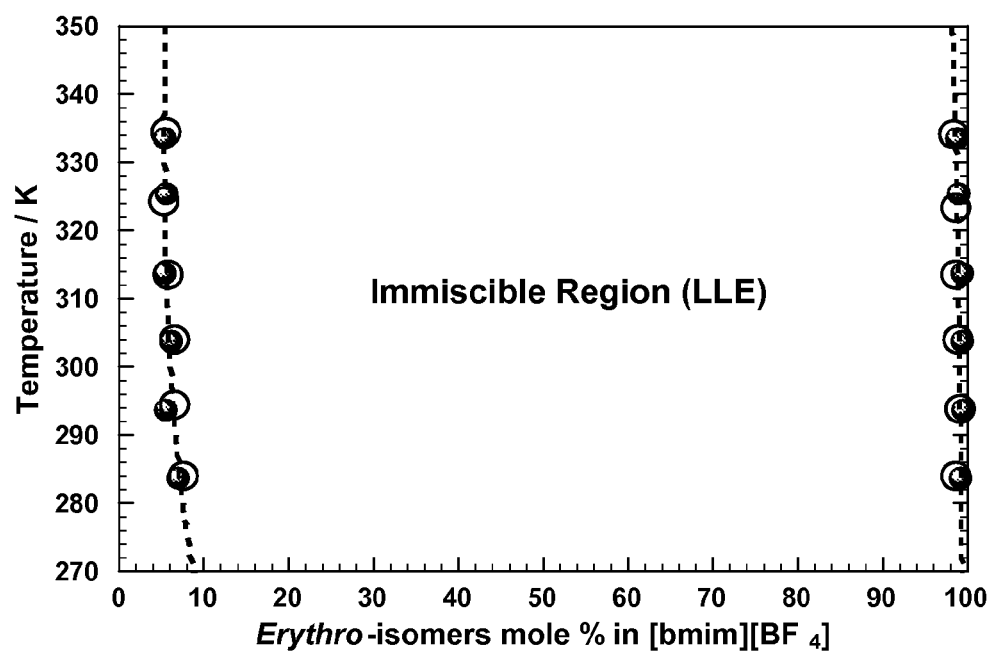
Figure 5A:
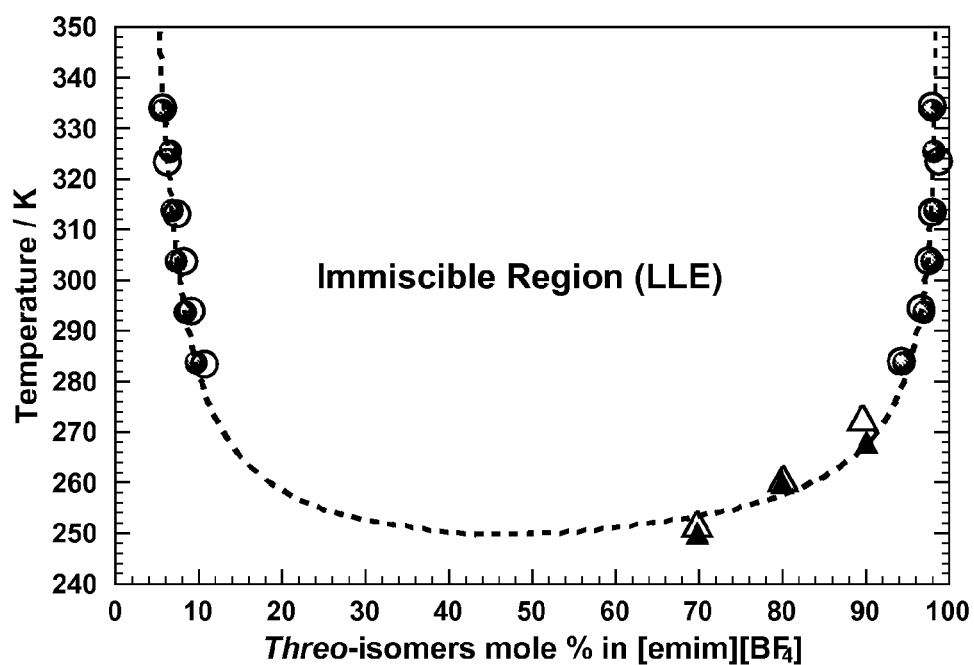
FIG. 5 shows Tx phase diagrams for LLE. Broken line: calculated with the NRTL activity model for non-deuterated species. Symbols: experimental data; solid symbols=non-deuterated species; open symbols=deuterated species; circles=LLE experiments and triangles=the cloud-point method. (a) Threo+[emim][$BF_4$] system. (b) Erythro+[emim][$BF_4$] system.
Figure 5B:
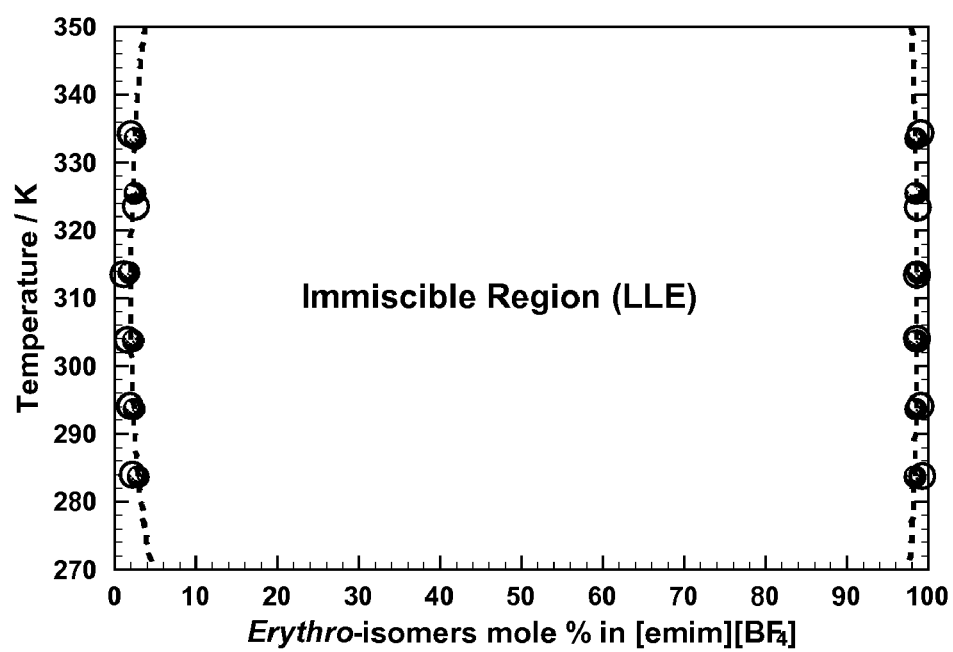

As shown in FIGS. 3-5, the threo (both deuterated and non-deuterated) isomers (or threo-D and threo-H isomers) are more soluble in the present ionic liquids than the erythro-D and erythro-H isomers.

In the case of all the threo isomer mixtures with ionic liquids, the LLE phase equilibria possess lower critical solution temperatures (LCSTs), as shown in FIGS. 3a, 4a, and 5a. However, in the case of the [emim][BF$_4$] binary systems, the LCST may be intercepted by a solid-liquid phase boundary, since the freezing point temperature of pure [emim][BF$_4$] is 287.6 K. The RTIL-rich side solutions below 280 K were not studied for the [emim][BF$_4$] system, since the solutions became extremely viscous and could not be thoroughly mixed in the experiment.

The present LLE data have been correlated by the NRTL activity model, as shown in FIGS. 3-5. The volumetric method used herein to determine LLE, which is based on Shiflett, M. B. and Yokozeki, A. (Vapor-liquid-liquid equilibria of pentafluoroethane and ionic liquid [bmim][PF$_6$] mixtures studied with the volumetric method, J. Phys. Chem. B (2006) 110:14436-14443); and on Shiflett, M. B. and Yokozeki, A. (Vapor-liquid-liquid equilibria of hydrofluorocarbons+1-butyl-3-methylimidazolium hexafluorophosphate, J. Chem. & Eng. Data (2006) 51:1931-1939), is typically applied to a binary system. As HFC-4310mee is a mixture of the threo- and erythro-isomers (about 88 vol % and 12 vol %, respectively), a mixture of HFC-4310mee and an ionic liquid is not a binary but ternary system, and the mixtures of HFC-4310mee and ionic liquids studied herein are thus ternary systems that have been treated as pseudo-binary systems. The experimental data has thus been analyzed and presented in Tables 1~3 on the basis of the treatment of mixtures of HFC-4310mee and ionic liquids as pseudo-binary systems.

EXAMPLE 1

Experimental Solubility Data for Mixtures of HFC-4310mee and 1-butyl-3-methylimidazolium hexafluorophosphate Experimental solubility (Tx) data for HFC-4310mee in 1-butyl-3-methylimidazolium hexafluorophosphate ([bmim][PF$_6$]) are summarized in Table 1. HFC-4310mee is abbreviated "HFC".

TABLE 1

| HFC-4310mee (1) + [bmim][PF$_6$] (2) system | | |
|---|---|---|
| T/K | Lower phase/ mol % HFC | Upper phase/ mol % HFC |
| HFC-4310mee Threo-H (1) + [bmim][PF$_6$] (2) | | |
| 294.8 ± 0.2 | 97.9 ± 0.7 | 27.1 ± 0.9 |
| 303.5 ± 0.2 | 98.6 ± 1.0 | 23.8 ± 0.8 |
| 313.7 ± 0.2 | 98.7 ± 1.0 | 21.1 ± 0.9 |
| 323.8 ± 0.2 | 98.9 ± 1.0 | 19.3 ± 1.5 |
| 333.3 ± 0.2 | 98.9 ± 1.1 | 18.3 ± 1.4 |
| HFC-4310mee Threo-D (1) + [bmim][PF$_6$] (2) | | |
| 293.7 ± 0.2 | 97.6 ± 0.6 | 26.7 ± 0.9 |
| 303.6 ± 0.2 | 98.7 ± 0.7 | 23.1 ± 1.0 |
| 314.2 ± 0.2 | 98.7 ± 1.0 | 21.1 ± 1.3 |

TABLE 1-continued

| HFC-4310mee (1) + [bmim][PF$_6$] (2) system | | |
|---|---|---|
| T/K | Lower phase/ mol % HFC | Upper phase/ mol % HFC |
| 323.9 ± 0.2 | 99.4 ± 0.9 | 19.3 ± 1.4 |
| 332.9 ± 0.2 | 99.2 ± 1.0 | 17.4 ± 1.5 |
| HFC-4310mee Erythro-H (1) + [bmim][PF$_6$] (2) | | |
| 282.6 ± 0.2 | 99.5 ± 0.5 | 8.2 ± 1.2 |
| 294.8 ± 0.2 | 99.4 ± 0.6 | 8.3 ± 1.1 |
| 303.5 ± 0.2 | 99.2 ± 0.5 | 8.6 ± 1.1 |
| 313.7 ± 0.2 | 98.7 ± 0.6 | 8.6 ± 1.4 |
| 323.8 ± 0.2 | 98.3 ± 0.7 | 7.6 ± 1.5 |
| 333.6 ± 0.2 | 98.2 ± 0.7 | 7.4 ± 1.2 |
| HFC-4310mee Erythro-D (1) + [bmim][PF$_6$] (2) | | |
| 283.7 ± 0.2 | 99.7 ± 0.3 | 8.6 ± 1.7 |
| 294.0 ± 0.2 | 99.6 ± 0.4 | 8.2 ± 1.7 |
| 303.9 ± 0.2 | 99.0 ± 0.5 | 9.3 ± 1.6 |
| 313.5 ± 0.2 | 99.0 ± 0.6 | 9.5 ± 1.8 |
| 323.5 ± 0.2 | 98.7 ± 0.6 | 8.7 ± 1.8 |
| 333.9 ± 0.2 | 98.8 ± 0.6 | 9.3 ± 1.9 |
| HFC-4310mee (1) + [bmim][PF$_6$] (2) | | |
| 286.6 ± 0.2 | 98.3 ± 0.7 | 21.3 ± 0.4 |
| 291.9 ± 0.2 | 98.8 ± 0.5 | 19.6 ± 0.5 |
| 298.3 ± 0.2 | 98.7 ± 0.5 | 18.9 ± 0.6 |
| 303.2 ± 0.2 | 98.5 ± 0.5 | 17.9 ± 0.7 |
| 313.5 ± 0.2 | 99.0 ± 0.6 | 16.6 ± 0.7 |
| 323.4 ± 0.2 | 98.9 ± 0.6 | 15.4 ± 0.7 |

EXAMPLE 2

Experimental Solubility Data for Mixtures of HFC-4310mee and 1-butyl-3-methylimidazolium tetrafluoroborate Experimental solubility (Tx) data for HFC-4310mee in 1-butyl-3-methylimidazolium tetrafluoroborate ([bmim][BF$_4$]) are summarized in Table 2. HFC-4310mee is abbreviated "HFC".

TABLE 2

| HFC-4310mee (1) + [bmim][BF$_4$] (2) system | | |
|---|---|---|
| T/K | Lower phase/ mol % HFC | Upper phase/ mol % HFC |
| HFC-4310mee Threo-H (1) + [bmim][BF$_4$] (2) | | |
| 313.6 ± 0.2 | 95.4 ± 0.8 | 40.6 ± 1.5 |
| 323.7 ± 0.2 | 98.1 ± 0.6 | 27.1 ± 1.1 |
| 334.1 ± 0.2 | 98.5 ± 0.6 | 21.8 ± 0.9 |
| HFC-4310mee Threo-D (1) + [bmim][BF$_4$] (2) | | |
| 313.6 ± 0.2 | 93.9 ± 0.7 | 46.8 ± 1.4 |
| 323.7 ± 0.2 | 97.5 ± 0.5 | 29.0 ± 1.0 |
| 334.1 ± 0.2 | 98.1 ± 0.6 | 23.1 ± 0.7 |
| HFC-4310mee Erythro-H (1) + [bmim][BF$_4$] (2) | | |
| 283.6 ± 0.2 | 99.2 ± 0.7 | 7.0 ± 1.1 |
| 293.6 ± 0.2 | 99.5 ± 0.8 | 5.5 ± 0.9 |
| 303.7 ± 0.2 | 99.4 ± 0.8 | 6.2 ± 1.3 |
| 313.7 ± 0.2 | 99.4 ± 0.8 | 5.4 ± 1.3 |
| 325.4 ± 0.2 | 99.0 ± 0.9 | 5.6 ± 1.1 |
| 333.5 ± 0.2 | 98.8 ± 1.0 | 5.4 ± 1.1 |
| HFC-4310mee Erythro-D (1) + [bmim][BF$_4$] (2) | | |
| 283.5 ± 0.2 | 99.2 ± 0.7 | 7.1 ± 1.2 |
| 294.1 ± 0.2 | 99.4 ± 0.7 | 6.5 ± 1.6 |
| 303.9 ± 0.2 | 99.0 ± 0.9 | 6.3 ± 1.3 |

TABLE 2-continued

HFC-4310mee (1) + [bmim][BF$_4$] (2) system

| T/K | Lower phase/ mol % HFC | Upper phase/ mol % HFC |
|---|---|---|
| 313.5 ± 0.2 | 98.9 ± 0.8 | 5.5 ± 1.5 |
| 323.4 ± 0.2 | 98.8 ± 0.8 | 5.3 ± 1.1 |
| 334.0 ± 0.2 | 98.7 ± 0.9 | 5.6 ± 1.3 |
| HFC-4310mee (1) + [bmim][BF$_4$] (2) | | |
| 313.7 ± 0.2 | 99.5 ± 0.5 | 24.5 ± 2.2 |
| 325.6 ± 0.2 | 98.6 ± 0.6 | 20.4 ± 0.8 |
| 333.5 ± 0.2 | 98.6 ± 0.6 | 17.6 ± 0.8 |

EXAMPLE 3

Experimental Solubility Data for Mixtures of mee and 1-ethyl-3-methylimidazolium tetrafluoroborate Experimental solubility (Tx) data for HFC-4310mee in 1-ethyl-3-methylimidazolium tetrafluoroborate ([emim][BF$_4$]) are summarized in Table 3. HFC-4310mee is abbreviated "HFC".

TABLE 3

HFC-4310mee (1) + [emim][BF$_4$] (2) system

| T/K | Lower phase/ mol % HFC | Upper phase/ mol % HFC |
|---|---|---|
| HFC-4310mee Threo-H (1) + [emim][BF$_4$] (2) | | |
| 283.6 ± 0.2 | 94.6 ± 0.7 | 9.7 ± 0.6 |
| 293.6 ± 0.2 | 97.0 ± 0.6 | 8.4 ± 0.7 |
| 293.6 ± 0.2 | 98.0 ± 0.7 | 7.3 ± 1.0 |
| 313.7 ± 0.2 | 98.3 ± 0.8 | 6.8 ± 0.8 |
| 325.4 ± 0.2 | 98.1 ± 1.1 | 6.1 ± 0.8 |
| 333.5 ± 0.2 | 98.0 ± 1.1 | 5.7 ± 1.0 |
| HFC-4310mee Threo-D (1) + [emim][BF$_4$] (2) | | |
| 283.7 ± 0.2 | 94.4 ± 0.4 | 10.5 ± 0.5 |
| 294.0 ± 0.2 | 96.8 ± 0.4 | 8.9 ± 0.7 |
| 303.8 ± 0.2 | 97.6 ± 0.7 | 8.0 ± 0.9 |
| 313.4 ± 0.2 | 97.9 ± 0.4 | 7.2 ± 1.0 |
| 323.5 ± 0.2 | 98.5 ± 0.6 | 6.2 ± 1.2 |
| 333.9 ± 0.2 | 97.8 ± 0.6 | 5.7 ± 1.4 |
| HFC-4310mee Erythro-H (1) + [emim][BF$_4$] (2) | | |
| 283.6 ± 0.2 | 98.4 ± 1.1 | 2.9 ± 1.2 |
| 293.6 ± 0.2 | 98.5 ± 1.3 | 2.4 ± 1.3 |
| 293.6 ± 0.2 | 98.6 ± 1.3 | 2.3 ± 1.5 |
| 313.7 ± 0.2 | 98.8 ± 1.2 | 1.8 ± 1.4 |
| 325.4 ± 0.2 | 98.5 ± 1.2 | 2.5 ± 1.3 |
| 333.5 ± 0.2 | 98.5 ± 1.4 | 2.5 ± 1.5 |
| HFC-4310mee Erythro-D (1) + [emim][BF$_4$] (2) | | |
| 283.9 ± 0.2 | 99.5 ± 0.5 | 2.0 ± 1.1 |
| 294.1 ± 0.2 | 99.0 ± 1.0 | 1.7 ± 1.5 |
| 303.9 ± 0.2 | 98.6 ± 1.2 | 1.5 ± 1.1 |
| 313.5 ± 0.2 | 98.7 ± 1.2 | 1.1 ± 1.0 |
| 323.4 ± 0.2 | 98.6 ± 1.1 | 2.5 ± 1.1 |
| 334.0 ± 0.2 | 99.1 ± 0.9 | 2.0 ± 1.1 |
| HFC-4310mee (1) + [emim][BF$_4$] (2) | | |
| 283.6 ± 0.2 | 97.7 ± 0.9 | 7.8 ± 0.8 |
| 293.6 ± 0.2 | 98.4 ± 0.9 | 6.4 ± 0.9 |
| 293.6 ± 0.2 | 99.0 ± 1.0 | 5.9 ± 0.9 |
| 313.7 ± 0.2 | 99.1 ± 1.0 | 5.4 ± 1.1 |
| 325.4 ± 0.2 | 98.8 ± 1.0 | 5.0 ± 1.1 |
| 333.5 ± 0.2 | 98.8 ± 1.0 | 5.0 ± 1.1 |

EXAMPLE 4

Cloud Point Measurements of HFC-4310mee+Ionic Liquids

Experimental solubility cloud point measurements of HFC-4310mee Threo-H and Threo-D (1)+Ionic Liquids (2) are summarized in Table 4.

TABLE 4

Cloud Point Measurements of HFC-4310mee Threo-H or Threo-D (1) Plus Ionic Liquid (2)

| T/K | mol % HFC |
|---|---|
| HFC-4310mee Threo-H (1) + [bmim][PF$_6$] (2) | |
| 270 ± 1 | 40.6 ± 0.5 |
| 269 ± 1 | 50.8 ± 0.5 |
| 268 ± 1 | 60.4 ± 0.5 |
| 265 ± 1 | 69.7 ± 0.5 |
| 264 ± 1 | 80.0 ± 0.5 |
| 276 ± 1 | 90.0 ± 0.5 |
| HFC-4310mee Threo-H (1) + [bmim][BF$_4$] (2) | |
| 311 ± 1 | 50.0 ± 0.5 |
| 309 ± 1 | 59.1 ± 0.5 |
| 308 ± 1 | 69.8 ± 0.5 |
| 307 ± 1 | 79.5 ± 0.5 |
| 308 ± 1 | 91.0 ± 0.5 |
| HFC-4310mee Threo-H (1) + [emim][BF$_4$] (2) | |
| 250 ± 3 | 69.8 ± 0.5 |
| 260 ± 2 | 80.0 ± 0.5 |
| 268 ± 1 | 90.1 ± 0.5 |
| HFC-4310mee Threo-D (1) + [bmim][PF$_6$] (2) | |
| 272 ± 1 | 40.0 ± 0.5 |
| 271 ± 1 | 50.0 ± 0.5 |
| 271 ± 1 | 59.7 ± 0.5 |
| 267 ± 1 | 69.8 ± 0.5 |
| 267 ± 1 | 79.7 ± 0.5 |
| 272 ± 1 | 88.5 ± 0.5 |
| HFC-4310mee Threo-D (1) + [bmim][BF$_4$] (2) | |
| — | — |
| 311 ± 1 | 59.9 ± 0.5 |
| 310 ± 1 | 69.4 ± 0.5 |
| 309 ± 1 | 80.1 ± 0.5 |
| 310 ± 1 | 89.3 ± 0.5 |
| HFC-4310mee Threo-D (1) + [emim][BF$_4$] (2) | |
| 252 ± 3 | 69.6 ± 0.5 |
| 261 ± 2 | 80.1 ± 0.5 |
| 273 ± 1 | 89.8 ± 0.5 |

EXAMPLE 5

Binary Interaction Parameters

Binary interaction parameters for equation 5 are summarized in Table 5.

TABLE 5

Binary Interaction Parameters in equation 5.

| System (1)/(2) | $\tau_{12}^{(0)}$ | $\tau_{12}^{(1)}/K$ | $\tau_{12}^{(2)}/K^{-1}$ | $\tau_{21}^{(0)}$ | $\tau_{21}^{(1)}/K$ | $\tau_{21}^{(2)}/K^{-1}$ |
|---|---|---|---|---|---|---|
| Threo/[bmim][PF$_6$] | 145.421 | −22306.3 | −0.22289 | −37.7767 | 5492.1 | 0.06485 |
| Erythro/[bmim][PF$_6$] | −5.2583 | 2803.2 | 0 | 2.97012 | −584.1 | 0 |
| Threo/[bmim][BF$_4$] | 91.1575 | −1463.8 | −0.12883 | 81.6624 | −1506.8 | −0.10921 |
| Erythro/[bmim][BF$_4$] | −1.1221 | 1492.7 | 0 | 18.7323 | −3018.8 | −0.02457 |
| Threo/[emim][BF$_4$] | 50.3746 | −7994.5 | −0.06965 | −7.2227 | 1138.3 | 0.01580 |
| Erythro/[emim] [BF$_4$] | 25.6965 | −3500.0 | −0.03688 | 72.2927 | −10850.0 | −0.11250 |

EXAMPLE 6

Figure 6A:
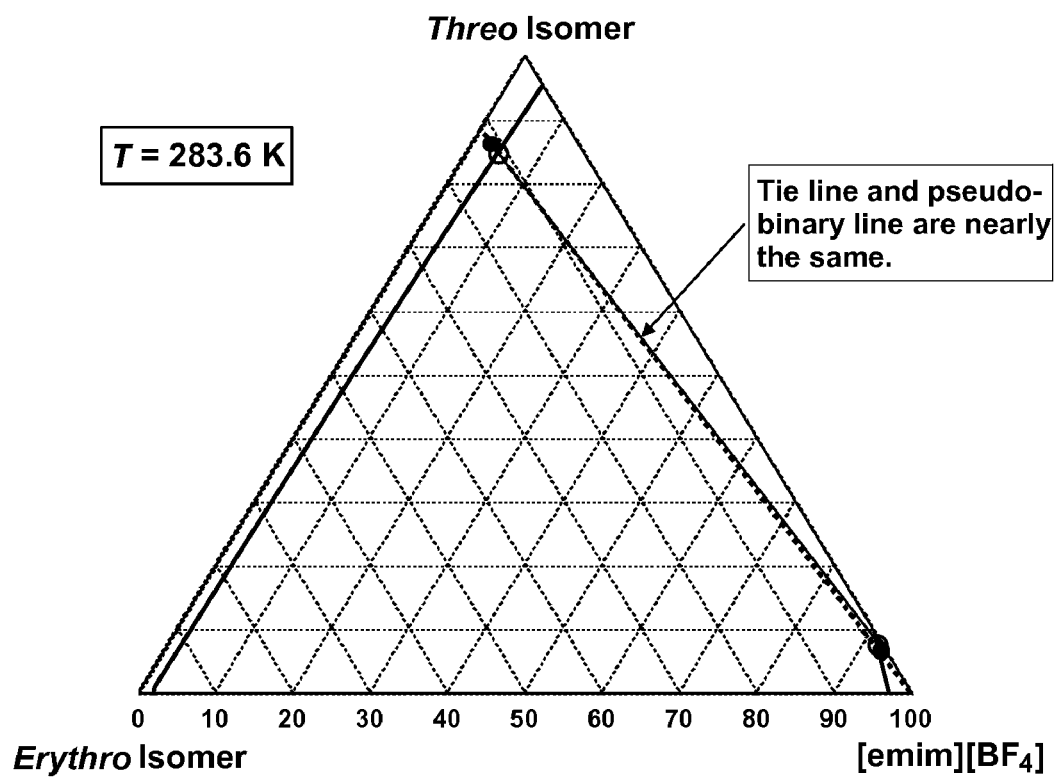
FIG. 6 shows ternary LLE phase diagrams. Thick solid lines: LLE boundaries calculated with the NRTL model. Thick broken line: pseudo-binary composition line for HFC-4310mee+room temperature ionic liquid (RTIL). Thin solid lines: calculated LLE tie lines. Solid circles=apparent experimental LLE data. Open circles=corrected LLE compositions. (a) Threo+Erythro+[emim][$BF_4$] system at 283.6 K. (b) Threo+Erythro+[bmim][$BF_4$] system at 313.7 K.
Figure 6B:
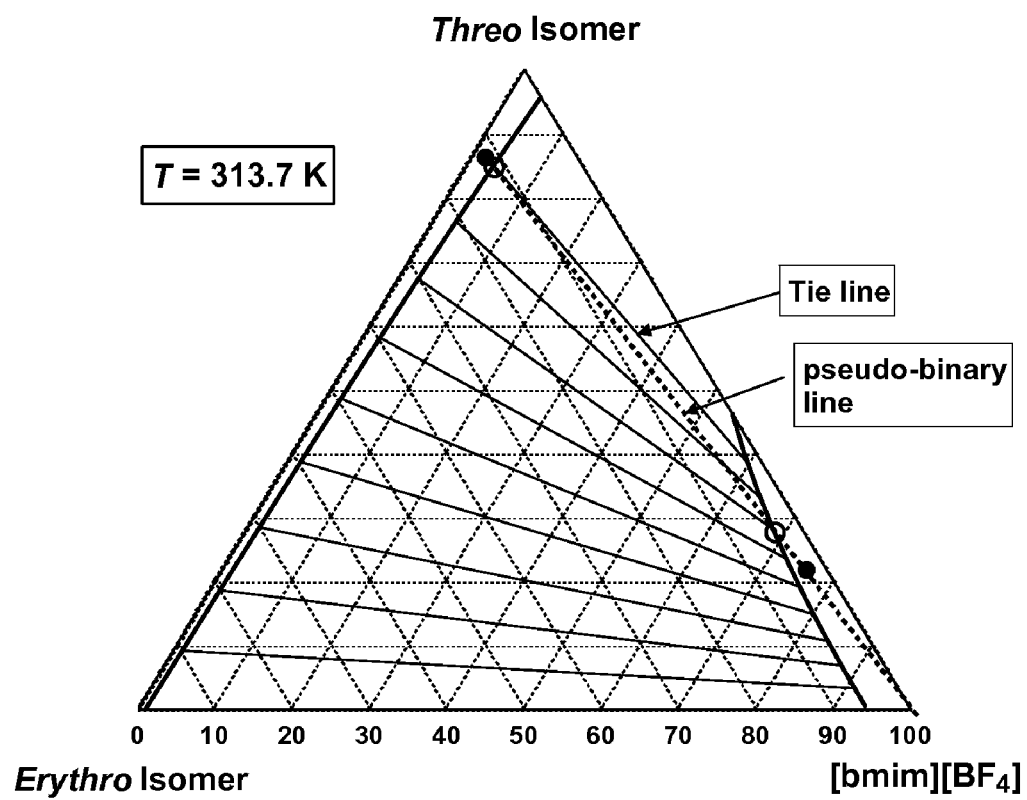

Separation of HFC-4310mee Diastereomers by Liquid-Liquid Extraction Using Ionic Liquids Ternary LLE phase diagrams have been constructed, using the binary interaction parameters provided in Example 5 to evaluate the separation of HFC-4310mee into the threo and erythro diastereomers. FIGS. 6a and 6b show two examples of constant T phase diagrams: threo+erythro+[emim][BF$_4$] and threo+erythro+[bmim][BF$_4$] systems. A single stage liquid-liquid extraction process is equivalent to an equilibrium stage and the countercurrent process can be represented on a ternary diagram such as FIG. 6a or 6b by connecting a line from the solvent stream inlet composition to the mixture stream inlet composition. The point where such a line crosses the LLE tie line provides the composition of the streams which leave the stage in equilibrium with the inlet streams. The exit compositions for the solvent and mixture can be determined by moving to the ends of the tie line where the tie line connects with the two phase boundary. The compositions at either end of the LLE tie line connecting the two phase boundary define the compositions which are representative of the exit stream compositions (see, in this connection, *Transport Processes and Unit Operations*, 2$^{nd}$ Edition, C. J. Geankoplis, section 12.5). When there is a separation of the diastereomers from HFC-4310mee (which is composed of approximately 88 vol % HFC-4310mee-threo and approximately 12 vol % HFC-4310mee-erythro) using [bmim][BF$_4$] as the extractant, the composition of the extract outlet stream will become enriched in the threo-diastereomer (92 vol % HFC-4310-mee-threo and 8 vol % HFC-4310-mee-erythro) compared with the initial feed composition. Multiple equilibrium stages are utilized to make an efficient separation and the number of stages is determined by the final purity required of the product.

To evaluate this characterization, a sample of HFC-4310mee was analyzed by gas chromatography and found to contain 88.8 vol % HFC-4310mee-threo and 11.2 vol % HFC-4310mee-erythro diastereomers. A 7.2 gram sample of HFC-4310mee (i.e., the feed) was mixed with 15.1 grams of [bmim][BF$_4$] (i.e., the extractant) in a separator funnel and vigorously mixed and then allowed to separate into two phases. The bottom phase (i.e., the raffinate) was rich in HFCs and the top phase (i.e., the extract) had a slight yellow color and was rich in [bmim] [BF$_4$]. The lower phase was separated from the top phase by opening the stopcock valve on the bottom of the separatory funnel and decanting off the lower phase. The remaining upper phase was analyzed by gas chromatography. The upper phase contained 91.8 vol % HFC-4310mee-threo and 8.2 vol % HFC-4310mee-erythro, which is in accordance with the ternary diagrams.

Based on the results shown above, a process for the separation of HFC-4310mee diastereomers by liquid-liquid extraction using ionic liquids in a liquid-liquid extraction column is described below. The liquid-liquid extraction may be achieved, for example, using crosscurrent extraction. A feed of HFC-4310mee [approximately 88 vol % HFC-4310mee-threo (abbreviated T) and approximately 12 vol % HFC-4310mee-erthryo (abbreviated E)] is contacted with the ionic liquid extractant [bmim][BF$_4$] in an equilibrium stage (as shown, for example, in FIG. 7). The extract is ionic liquid-rich and is enriched in HFC-4310mee threo (approximately 92 vol % threo isomer and 8 vol % erythro isomer, neglecting the amount of [bmim][BF$_4$]) relative to the raffinate. The raffinate is the lower liquid phase, which is HFC-rich. This is fed to a second equilibrium stage and contacted with fresh solvent. Again a separation occurs enriching the raffinate even further in HFC-4310mee-erythro. This process continues through N stages until the desired purity of the HFC-4310mee-erythro is achieved. It may be desired, for example, to employ 10 to 20 equilibrium stages such as described above when seeking to achieve purities greater than 99% HFC-4310mee-erythro.

Liquid-liquid extraction may also be achieved using countercurrent extraction. An extractant, [bmim] [BF$_4$], may be seen in FIG. 8 to enter the stage or end of the extraction column farthest from where a feed of HFC-4310mee [88 vol % HFC-4310mee-threo (abbreviated T) and 12 vol % HFC-4310mee-erthryo (abbreviated E)] enters, and the two phases pass countercurrently to each other. The extract is enriched in HFC-4310mee threo, and the raffinate is enriched in HFC-4310mee erythro as the two phases contact one another along the column. The total number of stages ("N") required is indicated by the desired purity of the erythro isomer.

What is claimed is:

1. A process for separating one diastereomer of dihydrodecafluoropentane from a mixture comprising at least one pair of diastereomers of dihydrodecafluoropentane, comprising contacting the mixture with a solvent consisting essentially of at least one ionic liquid in which one of the diastereomers is soluble to a greater extent than the other diastereomer, and separating the lower-solubility diastereomer from the mixture;

wherein an ionic liquid comprises a cation selected from the group consisting of the following eleven cations:

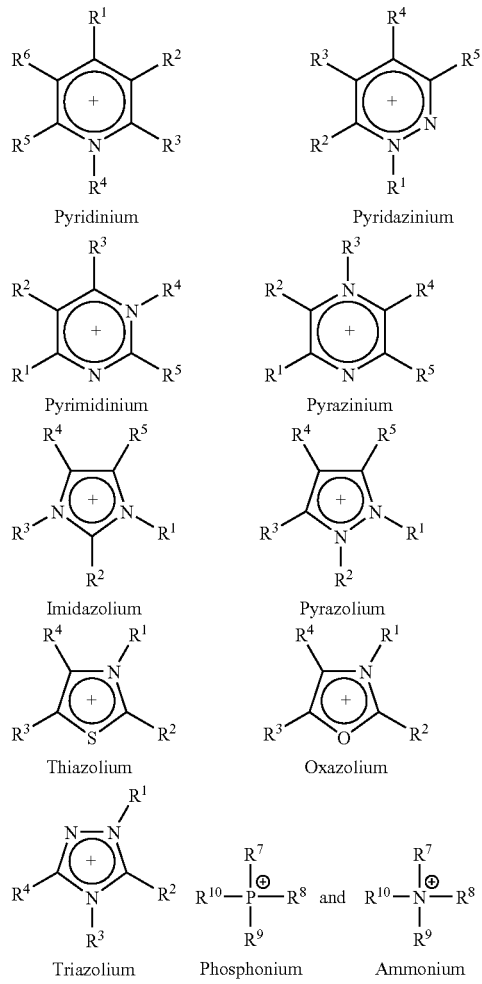

wherein $R^1$, $R^2$, $R^3$, $R^{4, R5}$, $R^6$ are independently selected from the group consisting of:
(i) H;
(ii) halogen;
(iii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(iv) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(v) $C_6$ to $C_{20}$ unsubstituted aryl, or $C_3$ to $C_{25}$ unsubstituted heteroaryl having one to three heteroatoms independently selected from the group consisting of O, N, Si and S; and
(vi) $C_6$ to $C_{25}$ substituted aryl, or $C_3$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
(1) —$CH_3$, —$C_2H_5$, or $C_3$ to $C_{25}$ straight-chain, branched or cyclic alkane or alkene, optionally substituted with at least one member selected from the group consisting of Cl, Br, F I, OH, $NH_2$ and SH,
(2) OH,
(3) $NH_2$, and
(4) SH;
$R^7$, $R^8$, $R^9$ and $R^{10}$ are independently selected from the group consisting of:
(vii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(viii) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(ix) $C_6$ to $C_{25}$ unsubstituted aryl, or $C_3$ to $C_{25}$ unsubstituted heteroaryl having one to three heteroatoms independently selected from the group consisting of O, N, Si and S; and
(x) $C_6$ to $C_{25}$ substituted aryl, or $C_3$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
(1) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH,
(2) OH,
(3) $NH_2$, and
(4) SH; and
wherein, optionally, at least two of $R^1$, $R^2$, $R^3$, $R^4$, $R^5$, $R^6$, $R^7$, $R^8$, $R^9$ and $R^{10}$ together form a cyclic or bicyclic alkanyl or alkenyl group; and
an anion selected from the group consisting of $[CH_3CO_2]$—, $[HSO_4]$—, $[CH_3OSO_3]$—, $[C_2H_5OSO_3]$—, $[AlCl_4]$—, $[CO_3]^{2-}$, $[HCO_3]$—, $[NO_2]$—, $[NO_3]$—, $[SO_4]^{2-}$, $[PO_4]^{3-}$, $[HPO_4]^{2-}$, $[H_2PO_4]$—, $[HSO_3]$—, $[CuCl_2]$—, Cl—, Br—, I—, SCN—, and any fluorinated anion.

2. A process according to claim 1 wherein the lower solubility diastereomer comprises the HFC-4310mee threo diastereomer.

3. A process according to claim 1 wherein the lower solubility diastereomer comprises the HFC-4310mee erythro diastereomer.

4. A process according to claim 1 wherein at least one of $R^1$, $R^2$, $R^3$, $R^4$, $R^5$, $R^6$, $R^7$, $R^8$, $R^9$ and $R^{10}$ comprises F—.

5. A process according to claim 1 wherein an ionic liquid comprises an imidazolium cation.

6. A process according to claim 1 wherein an ionic liquid comprises a cation selected from 1-ethyl-3-methylimidazolium and 1-butyl-3-methylimidazolium.

7. A process according to claim 1 wherein an ionic liquid comprises an anion selected from the group consisting of $[BF_4]$—, $[PF_6]$—, $[SbF_6]$—, $[CF_3SO_3]$—, $[HCF_2CF_2SO_3]$—, $[CF_3HFCCF_2SO_3]$—, $[HCClFCF_2SO_3]$—, $[(CF_3SO_2)_2N]$—, $[(CF_3CF_2SO_2)_2N]$—, $[(CF_3SO_2)_3C]$—, $[CF_3CO_2]$—, and F—.

8. A process according to claim 1 wherein an ionic liquid comprises an anion selected from the group consisting of $[BF_4]$— and $[PF_6]$—.

9. A process according to claim 1 which is performed by liquid-liquid extraction.

10. A process according to claim 1 which is performed in a single-stage separation device.

11. A process according to claim 1 which is performed in a multi-stage separation device.

12. A process according to claim 1 which is performed in a crosscurrent separation device.

13. A process according to claim 1 which is performed in a countercurrent separation device.

14. A process according to claim 1 which is performed at a temperature of about 280 Kelvin to about 350 Kelvin.

15. A process according to claim 1 wherein an ionic liquid comprises an imidazolium cation, and/or an ionic liquid comprises an anion selected from the group consisting of $[CH_3CO_2]-$, $[HSO_4]-$, $[CH_3OSO_3]-$, $[C_2H_5OSO_3]-$, $[AlCl_4]-$, $[CO_3]^{2-}$, $[HCO_3]-$, $[NO_2]-$, $[NO_3]$, $[SO_4]^{2-}$, $[PO_4]^{3-}$, $[HPO_4]^{2-}$, $[H_2PO_4]-$, $[HSO_3]-$, $[CuCl_2]-$, $Cl-$, $Br-$, $I-$, $SCN-$, and any fluorinated anion.

16. A process for performing an industrial operation selected from the group consisting of a calibration operation, a cleaning operation, a rinsing operation, a drying operation, a particulate removal operation, a solvent operation, a dispersion operation, a heat transfer operation, and an insulating operation, comprising (a) contacting a mixture comprising a pair of diastereomers of dihydrodecafluoropentane with a solvent that consists essentially of at least one ionic liquid in which one of the diastereomers is soluble to a greater extent than the other diastereomer, (b) separating the lower-solubility diastereomer from the mixture, and (c) employing the separated diastereomer in the operation;

wherein an ionic liquid comprises a cation selected from the group consisting of the following eleven cations:

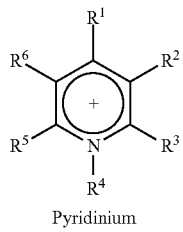
Pyridinium

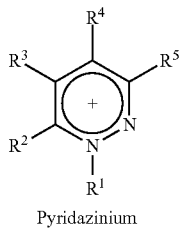
Pyridazinium

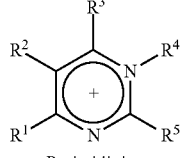
Pyrimidinium

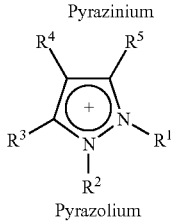
Pyrazinium

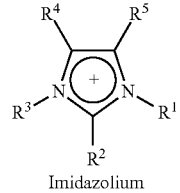
Imidazolium

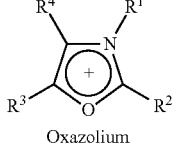
Pyrazolium

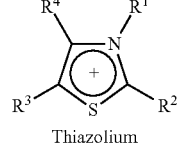
Thiazolium

Oxazolium

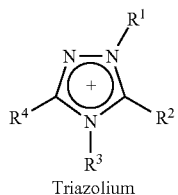
Triazolium

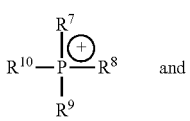
Phosphonium and

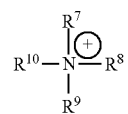
Ammonium wherein $R^1$, $R^2$, $R^3$, $R^4$, $R^5$ and $R^6$ are independently selected from the group consisting of:

(i) H;

(ii) halogen;

(iii) $-CH_3$, $-C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;

(iv) $-CH_3$, $-C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;

(v) $C_6$ to $C_{20}$ unsubstituted aryl, or $C_3$ to $C_{25}$ unsubstituted heteroaryl having one to three heteroatoms independently selected from the group consisting of O, N, Si and S; and (vi) $C_6$ to $C_{25}$ substituted aryl, or $C_3$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:

(1) $-CH_3$, $-C_2H_5$, or $C_3$ to $C_{25}$ straight-chain, branched or cyclic alkane or alkene, optionally substituted with at least one member selected from the group consisting of Cl, Br, F, I, OH, $NH_2$ and SH, (2) OH, (3) $NH_2$, and (4) SH;

$R^7$, $R^8$, $R^9$ and $R^{10}$ are independently selected from the group consisting of:

(vii) $-CH_3$, $-C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;

(viii) $-CH_3$, $-C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;

(ix) $C_6$ to $C_{25}$ unsubstituted aryl, or $C_3$ to $C_{25}$ unsubstituted heteroaryl having one to three heteroatoms independently selected from the group consisting of O, N, Si and S; and (x) $C_6$ to $C_{25}$ substituted ary, or $C_3$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
- (1) —CH$_3$, —C$_2$H$_5$, or C$_3$ to C$_{25}$ straight-chain, branched or cyclic alkane or alkene, optionally substituted with at least one member selected from the group consisting of Cl, Br, F, I, OH, NH$_2$ and SH,
- (2) OH,
- (3) NH$_2$, and
- (4) SH; and wherein, optionally, at least two of R$^1$, R$^2$, R$^3$, R$^4$, R$^5$, R$^6$, R$^7$, R$^8$, R$^9$ and R$^{10}$ together to form a cyclic or bicyclic alkanyl or alkenyl group; and an anion selected from the group consisting of [CH$_3$CO$_2$]—, [HSO$_4$]—, [CH$_3$OSO$_3$]—, [C$_2$H$_5$OSO$_3$]—, [AlCl$_4$]—, [CO$_3$]$^2$—, [HCO$_3$]—, [NO$_2$]—, [NO$_3$]—, [SO$_4$]$^2$—, [PO$_4$]$^3$—, [HPO$_4$]$^2$—, [H$_2$PO$_4$]—, [HSO$_3$]—, [CuCl$_2$]—, Cl—, Br—, I—, SCN—, and any fluorinated anion

17. A process according to claim 16 wherein the pair of diastereomers comprises HFC-4310mee threo and HFC-4310mee erythro.

* * * * *